(12) United States Patent
Mackenzie et al.

(10) Patent No.: US 11,579,093 B2
(45) Date of Patent: Feb. 14, 2023

(54) OPTICAL COMPONENT

(71) Applicant: SciLogica Corp., Denver, CO (US)

(72) Inventors: Alasdair Allan Mackenzie, Herefordshire (GB); Barry Colin Crane, Oxon (GB); Nicholas Paul Barwell, Warwickshire (GB); Robert Perkins, Oxfordshire (GB); Praveen Sagar, Bucks (GB)

(73) Assignee: SciLogica Corp., Denver, CO (US)

( * ) Notice: Subject to any disclaimer, the term of this patent is extended or adjusted under 35 U.S.C. 154(b) by 269 days.

(21) Appl. No.: 16/855,707

(22) Filed: Apr. 22, 2020

(65) Prior Publication Data

US 2021/0333213 A1 Oct. 28, 2021

(51) Int. Cl.
| | |
|---|---|
| *G01N 21/77* | (2006.01) |
| *B29D 11/00* | (2006.01) |
| *G01N 21/64* | (2006.01) |
| *G01N 33/49* | (2006.01) |
| *G01N 21/75* | (2006.01) |

(52) U.S. Cl.
CPC ..... *G01N 21/7703* (2013.01); *B29D 11/0074* (2013.01); *G01N 21/6486* (2013.01); *G01N 33/49* (2013.01); *G01N 2021/757* (2013.01); *G01N 2021/7786* (2013.01); *G01N 2201/0612* (2013.01); *G01N 2201/08* (2013.01)

(58) Field of Classification Search
CPC ....... G01N 2021/7786; G01N 21/6486; G01N 21/7703; G01N 33/49; G01N 2201/0612; G01N 2201/08; G01N 2021/757
See application file for complete search history.

(56) References Cited

U.S. PATENT DOCUMENTS

| | | | |
|---|---|---|---|
| 5,284,775 A | 2/1994 | Yafuso et al. | |
| 2006/0099327 A1 | 5/2006 | Horn et al. | |
| 2008/0131646 A1* | 6/2008 | Tanaka | B32B 27/08 |
| | | | 526/348 |
| 2010/0280184 A1 | 11/2010 | Crane | |
| 2012/0153311 A1* | 6/2012 | Yuan | F21K 9/90 |
| | | | 264/2.7 |
| 2015/0174231 A1 | 6/2015 | Giuliani et al. | |

FOREIGN PATENT DOCUMENTS

| | | | |
|---|---|---|---|
| EP | 2573548 A1 | 3/2013 | |
| WO | WO-0179821 A1 * | 10/2001 | ......... G01N 21/6428 |

(Continued)

OTHER PUBLICATIONS

European Search Repod received for Application No. EP20172909.2, Search completed on Sep. 2, 2020.

(Continued)

*Primary Examiner* — Thomas A Hollweg
*Assistant Examiner* — Mary A El-Shammaa
(74) *Attorney, Agent, or Firm* — Harness, Dickey & Pierce, P.L.C.

(57) ABSTRACT

The invention is concerned with methods for producing a useful and highly uniform optical component which is useful in the construction of an optical sensor. Also discussed are the optical component itself, an optical sensor comprising the optical component, a process for producing the optical sensor and a process for detecting and/or quantifying the amount of an analyte in a sample using the optical sensor.

25 Claims, 4 Drawing Sheets

(56) References Cited

FOREIGN PATENT DOCUMENTS

| WO | WO-02079765 A2 | * | 10/2002 | ........... G01N 21/552 |
| WO | WO-2020097268 A1 | * | 5/2020 | ............. G01N 21/77 |

OTHER PUBLICATIONS

Hetemi and Pinson (2017) Chem. Soc. Rev. 46, 5701-5713.
Drobota et al. (2013) Cent. Eur. J. Chem 11(11), 1786-1798.
Nguyen et al. (2009) Proc. of SPIE 7503, 750314-1.
Lin et al. (2009) Organic Letters 11,4858-4861.
Fusa & He (2005) J. mater. Chem. 15, 2640-2647.
De Silva et al. (2008) Org. Biomol. Chem. 6, 2468-2481.
Lee et al. (2009) Anal. Chem. 81, 538.
Martinez-Zaguilan et al. (1998) Cell Physiol. Biochem. 8,158.
Ge et al. (2003) Biosensors and Bioelectronics 18, 857-865.
Ge et al. (2012) Analytica Chimica Acta 734, 79-87.
Chu and Lo (2011) Sensors and Actuators B, 155, 53-57.
Escobedo et al. (2017) Anal. Chem. 89, 1697-1703.
Chu et al. (2011) Photonic Sensors 1(3), 234-250.
Invitrogen (2010) The Molecular Probes Handbook: A guide to Fluorescent Probes and Labeling Technologies, 11th Edition Chapter 20 pp. 885-902.
Crane et al. (2015) Journal of Diabetes Science and technology 9, 751-761.
Le Goff et al. (2004) Anal. Chim. Acta 510, 175-182.

* cited by examiner

OPTICAL COMPONENT

FIELD OF THE INVENTION

Provided herein are methods for producing a useful and highly uniform optical component. Also provided are the optical component itself, an optical sensor comprising the optical component, a process for producing the optical sensor and a process for detecting and/or quantifying the amount of an analyte in a sample using the optical sensor.

BACKGROUND TO THE INVENTION

Optical sensors are now widely used to detect and quantify the presence of analytes in a wide variety of technical fields, including environmental chemistry, food hygiene and medicine. An optical sensor for detecting an analyte comprises a chemical system including a luminescent compound (typically a fluorophore) whose absorption and/or emission spectrum is altered by the presence of an analyte. For instance, the fluorophore may have a characteristic emission spectrum which alters when the luminescent compound interacts with the analyte. Thus, monitoring the absorption and/or emission of the luminescent compound (at a specific wavelength or across a range of wavelengths) as it is brought into contact with a sample can indicate whether or not a particular analyte is present in the sample.

By way of example, one luminescent compound is the commercially available Mag-fluo-4 fluorescent compound. Mag-fluo-4 is essentially non-fluorescent in the absence of divalent cations. However, in the presence of $Mg^{2+}$ cations, Mag-fluo-4 becomes strongly fluorescent, with a maximum fluorescence intensity at wavelengths of just under 520 nm. Thus, detection of fluorescence emission from Mag-fluo-4 can indicate the presence of magnesium ions.

Optical detection systems have particular advantages in the detection and quantification of analytes. They are often very specific to a particular analyte and resistant to interference from other species, as they will typically only interact with a specific analyte or group of analytes. Further, they can be calibrated to accurately indicate the quantity of analyte present in a sample. They can be used to provide rapid and continuous measurements. Moreover, optical sensors are equilibrium sensors which do not consume the analyte they are measuring or generate by-products. This is in contrast to electrochemical sensors which consume analyte and so rely on an unchanging rate of diffusion of the analyte to the sensor electrode in order to provide an accurate measurement.

However, luminescent compounds normally cannot simply be dispersed within a sample (for instance a food sample or a biological sample), not least because they may be harmful to consumers or patients. Thus, the luminescent compounds must be immobilised somehow in order to provide a useful sensor.

One method that has been used to immobilise luminescent compounds is to immobilise them within a polymer matrix in the sensor. To manufacture the sensor, the polymer matrix is typically provided at the end of an optical waveguide (usually an optical fibre) which directs incident light towards the sensing region containing the polymer, and directs emitted light away from the sensing region towards a detector.

There are significant practical difficulties associated with providing a polymer comprising the luminescent compound in the sensing region. In practice, an end of an optical fibre is often coated with a monomer solution and the polymer is generated in situ on the optical fibre. This is often done when the sensor is already assembled, as the optical fibre can be difficult and messy to handle once coated. Consequently, if any error is made during the procedure the entire sensor is rendered unusable.

This solution is unsatisfactory for several reasons. Firstly, the process is uneconomical. The individual coating of each optical waveguide is slow and labour-intensive. It requires the preparation of excess quantities of polymer solution, causing wastage of expensive luminescent compounds. Moreover, the procedure is difficult and errors are easily made, which can cause large fractions of the sensors made this way to be faulty (for instance if the polymerisation step is imperfectly performed or if the sensor is contaminated by spreading of the polymer outside the sensing region).

Perhaps even more significantly, the procedure is problematic because it must be performed separately upon each optical waveguide (usually an optical fibre) that is used. This means that uniformity of the sensing region cannot be guaranteed, and so each sensor (or where a sensor comprises more than one waveguide, each waveguide within the sensor) must be calibrated individually. This process is laborious.

Accordingly, there remains a need for an improved process for generating an optical component which comprises an immobilised luminescent compound. Such an improved process would ideally be:

i. more efficient, for instance able to generate multiple components simultaneously; and/or
ii. capable of providing uniform components, meaning that not all of the components need to be quality-tested and even calibrated individually; and/or
iii. less wasteful of polymer and/or luminescent compound; and/or
iv. more economic, for instance scalable to produce large quantities of the optical components.

It is also desirable to provide an optical component carrying a luminescent compound which is separable from the other parts of an optical sensor such as an optical waveguide (e.g. an optical fibre). It is also desirable to provide a process which generates such an optical component. This would enable the optical component carrying the immobilised luminescent compound to be tested before the sensor is assembled and, in case of any difficulties, discarded without causing the loss of an entire sensor assembly.

SUMMARY OF THE INVENTION

The inventors have provided an advantageous method of producing an optical component which addresses the above difficulties. The inventors have found that the polymer can be attached to an optically transmissive substrate, and then manipulated together with the substrate, for instance in the form of an optical component which can be easily added to, and removed from, an optical sensor apparatus. The inventors have found that a suitable optical component can be formed by chemically attaching a polymeric layer to the surface of the optically transmissive substrate. This chemical binding has been achieved by functionalising the surface and chemically binding a polymer to the surface. Accordingly, the invention provides a process for producing an optical component, the process comprising:

a) providing a substrate which is optically transmissive and which has a surface;
b) functionalising the surface of the substrate to produce surface functional groups thereon; and c) providing a polymeric layer comprising a polymer chemically bound to the surface functional groups, wherein a luminescent compound is immobilised within the polymeric layer.

The substrate is not especially limited as to its size. Accordingly, the process is highly scalable as it can be used to produce a large substrate from which many optical components can be cut out.

The inventors have further found that, where a polymer is provided on a substrate, and multiple optical components are cut from the substrate, the optical components have excellent uniformity. For instance, they can each comprise a polymeric layer of identical thickness and identical composition. The high uniformity of the components means that they can be used to create a batch of optical sensors wherein only one sensor, or a small percentage of the batch of sensors, must be tested and calibrated. Accordingly, the invention provides a process for producing a plurality of optical components, the process comprising:
a) providing a substrate which is optically transmissive and which has a surface;
b) providing a polymeric layer of uniform thickness on the surface, wherein a luminescent compound is immobilised within the polymeric layer; and
c) cutting two or more optical components from the substrate.

The invention also encompasses an optical component such as can be produced by chemically binding a polymer to the surface of an optically transmissive substrate. In particular, the invention provides an optical component comprising: an optically transmissive substrate which has a surface; a polymeric layer comprising a polymer chemically bound to surface functional groups on the surface; and a luminescent compound immobilised within the polymeric layer.

The optical components are much easier to manipulate than the polymer itself and can be easily added to, and removed from, an end of an optical waveguide in an optical sensor. Thus, the optical component can advantageously be used to provide an optical sensor. In one embodiment, therefore, the invention provides an optical sensor comprising:
an optical component as described herein; and
an optical waveguide arranged to direct light onto the optical component.

The optical sensor is easier to manufacture than optical sensors discussed in the prior art, because the polymeric layer wherein the luminescent compound is immobilised can be produced separately from the rest of the sensor. Accordingly the invention provides a process for producing an optical sensor as described herein, the process comprising:
providing an optical component comprising a substrate, a polymeric layer and a luminescent compound within the polymeric layer by a process as described herein; and
arranging an optical waveguide to direct light onto the optical component.

The optical sensor described herein can be used in a process for detecting and/or quantifying the amount of an analyte in a sample, the process comprising:
contacting an optical sensor as described herein with an analyte;
providing excitation light to the luminescent compound through the optical waveguide; and
detecting luminescent light emitted from the luminescent compound through the optical waveguide.

DETAILED DESCRIPTION OF THE INVENTION

Figure 1:
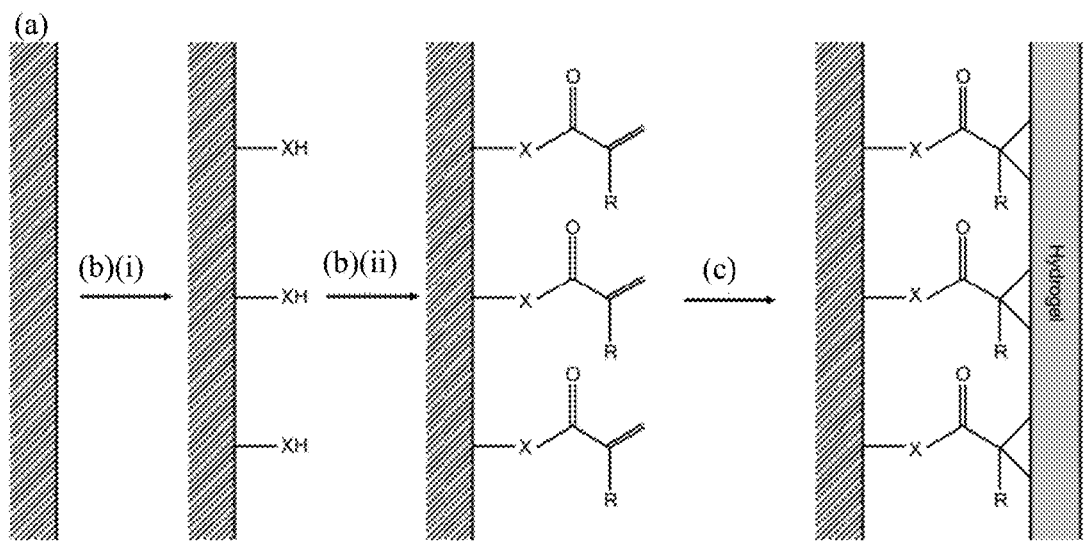
FIG. 1 provides a schematic representation of an embodiment of the process for producing an optical component described herein.

Unless defined otherwise, all technical and scientific terms used herein have the same meanings as commonly understood by one of skill in the relevant art.

The invention is described hereafter with reference to particular embodiments and drawings. However, the invention is not limited to any specific embodiment or aspect of the following description.

Those skilled in the art will recognize, or be able to ascertain using no more than routine experimentation, many equivalents to the specific embodiments of the invention described herein. Such equivalents are intended to be encompassed by the following claims.

Definitions

As used in this specification and the appended claims, the singular forms "a", "an", and "the" include plural referents unless the content clearly dictates otherwise. Thus, for example, reference to "a counter-ion moiety" includes two or more counter-ion moieties.

Where the term "comprising" is used in the present description and claims, it does not exclude other elements or steps. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Alkyl" as used herein refers to monovalent straight-chained and branched alkyl groups. Typically, the alkyl group is a straight-chained alkyl group. An alkyl group may have from 1 to 30 carbon atoms (i.e. is a $C_{1-30}$ alkyl group). Typically, an alkyl group is a $C_{1-20}$ alkyl group or a $C_{1-10}$ alkyl group. Preferred alkyl groups include $C_{1-6}$ alkyl groups, for example $C_{1-4}$ alkyl groups. Examples of alkyl groups include methyl and ethyl groups, and straight-chained or branched propyl, butyl and pentyl groups. Particular alkyl groups include methyl, ethyl, n-propyl, isopropyl, n-butyl, sec-butyl, isobutyl, and tert-butyl groups.

"Alkenyl" as used herein refers to a monovalent hydrocarbon moiety comprising one or more carbon-carbon double bonds. Typically an alkenyl group contains one carbon-carbon double bond. The hydrocarbon moiety may be a straight-chain or branched; typically, the hydrocarbon moiety is a straight chain. An alkenyl group may have from 2 to 30 carbon atoms (i.e. is a $C_{2-30}$ alkenyl group). Typically, an alkenyl group is a $C_{2-20}$ or a $C_{2-10}$ alkenyl group. Preferred alkenyl groups include $C_{2-6}$ alkenyl groups, for example $C_{2-4}$ alkenyl groups.

"Alkynyl" as used herein refers to a monovalent hydrocarbon moiety comprising one or more carbon-carbon triple bonds. Typically an alkynyl group contains one carbon-carbon triple bond. The hydrocarbon moiety may be a straight-chain or branched; typically, the hydrocarbon moiety is a straight chain. An alkynyl group may have from 2 to 30 carbon atoms (i.e. is a $C_{2-30}$ alkynyl group). Typically, an alkynyl group is a $C_{2-20}$ or a $C_{2-10}$ alkynyl group. Preferred alkynyl groups include $C_{2-6}$ alkynyl groups, for example $C_{2-4}$ alkynyl groups.

"Alkyloxy" as used herein refers to a monovalent group of the formula —O-alkyl, wherein the alkyl group is as described herein. Examples of alkyloxy groups include —O—$C_{1-6}$ alkyl groups, such as —$OCH_3$ and —$OCH_2CH_3$.

"Alkylene" as used herein refers to a divalent saturated hydrocarbon moiety which may be straight-chained or branched. Typically, the alkylene group is a straight-chained alkylene group. An alkylene group typically has from 1 to 10 carbon atoms (i.e. is a $C_{1-10}$ alkylene group). However, preferred alkylene groups include $C_{1-6}$ alkylene groups, for example $C_{1-4}$ alkylene groups. Examples of alkyl groups include methylene (—$CH_2$—) and ethylene (—$CH_2CH_2$—) groups.

"Alkenylene" as used herein refers to a divalent hydrocarbon moiety comprising one or more carbon-carbon double bonds. Typically an alkenylene group contains one carbon-carbon double bond. The hydrocarbon moiety may be a straight-chain or branched; typically, the hydrocarbon moiety is a straight chain. An alkenylene group typically has from 2 to 10 carbon atoms (i.e. is a $C_{2-10}$ alkenylene group). However, preferred alkenylene groups include $C_{2-6}$ alkenylene groups, for example $C_{2-4}$ alkenylene groups.

"Alkynylene" as used herein refers to a divalent hydrocarbon moiety comprising one or more carbon-carbon triple bonds. Typically an alkynylene group contains one carbon-carbon triple bond. The hydrocarbon moiety may be a straight-chain or branched; typically, the hydrocarbon moiety is a straight chain. An alkynylene group typically has from 2 to 10 carbon atoms (i.e. is a $C_{2-10}$ alkenylene group). However, preferred alkynylene groups include $C_{2-6}$ alkynylene groups, for example $C_{2-4}$ alkynylene groups.

The term "halogen" as used herein is intended to include fluorine, chlorine, bromine and iodine atoms, typically fluorine, chlorine or bromine.

Reference herein to a group in its protonated form should be taken to encompass reference to any deprotonated form which may be produced in solution. For instance, reference to "hydroxy" or "—COOH" should be taken to encompass such groups when deprotonated to —$O^-$ or —$COO^-$ in solution.

Functionalisation Step

The process for producing the optical component involves functionalising the surface of the substrate. The functionalisation step has been found to be useful in enabling the optically transmissive substrate to adhere firmly to the polymeric layer to provide a product which can be manipulated (for instance cut) easily, without displacing the polymer.

Functionalisation produces surface functional groups on the surface of the substrate. Surface functional groups are groups which are capable of attachment to the polymeric layer, for example by one or more covalent bonds. Surface functional groups will be defined in more detail below.

The functionalisation process, (b), may comprise one or more stages. In some embodiments, step (b) is a one-stage process. In other embodiments, step (b) comprises two or more stages.

A wide variety of processes for producing surface functional groups on a substrate are available. Suitable processes are described in "Surface functionalisation of polymers", Chem. Soc. Rev., D. Hetemi and J. Pinson, and in "Chemical modification and characterization of poly(ethylene terephthalate) surfaces for collagen immobilisation", Drobota et al., Cent. Eur. J. Chem., 11(11), 2013, 1786-1798; both of these papers are incorporated herein by reference in their entirety.

In one example, functionalising the surface of the substrate to produce surface functional groups comprises exposing the surface of the substrate to a plasma. A plasma is a gas comprising ionised species and electrons, possibly together with other highly reactive species. For example, an oxygen plasma comprise excited radicals and ions derived from oxygen. Plasmas can be produced by a variety of methods well-known in the art, for instance using a plasma arc machine. Functionalisation of surfaces using plasmas is discussed in "Surface functionalisation of polymers" (Hetemi & Pinson). The plasma is sufficiently reactive to generate reactive species will the generally unreactive surface of the substrate.

The plasma may typically comprise one or more of oxygen, alcohols, nitrogen, amines and hydrogen. For example, the plasma may comprise one or more of oxygen, methanol, ethanol, nitrogen, ammonia, methylamine, ethylamine, and hydrogen.

A plasma comprising oxygen can produce hydroxyl, alkyloxy and carboxyl surface functional groups on the surface of the substrate. It can also produce deprotonated groups, such as —$O^-$ and —$COO^-$.

A plasma containing nitrogen, ammonia or amines can produce amine surface functional groups on the surface of the substrate, for example —$NH_2$, —$NHCH_3$, —$N(CH_3)_2$, —$NHCH_2CH_3$, —$N(CH_3)(CH_2CH_3)$ and —$N(CH_2CH_3)_2$. In particular, a plasma comprising nitrogen and hydrogen can produce —$NH_2$ surface functional groups.

Functionalising the surface of the substrate may alternatively or additionally comprise treating the surface with a reactive chemical species. For instance, functionalising the surface may comprise treating the surface with an oxidant. An exemplary oxidant is a combination of sulphuric acid and a permanganate salt, such as potassium permanganate. Functionalisation of the surface with an oxidant can produce surface hydroxyl and carboxyl groups.

Functionalising the surface may comprise chemically etching the surface. For instance, a surface may be etched with a hydroxide solution such as sodium hydroxide solution; this typically produces hydroxyl groups on the surface and is particularly used where the substrate is a silica-based substrate such as glass.

In another example of chemical etching, functionalising the surface of the substrate may comprise aminolysing the surface. In an aminolysis process, the substrate is treated with a multifunctional amine. A multifunctional amine is a compound of formula $NH_2-(NH\text{-alkylene-})_n NH_2$ where n is a positive integer, or a derivative thereof. Suitable examples of a multifunctional amine are triethylenetetramine or a derivative thereof, or tetraethylenepentamine or a derivative thereof. Aminolysis produces amine surface functional groups on the surface of the substrate, such as $-NH_2$, $-NHCH_3$, $-N(CH_3)_2$, $-NHCH_2CH_3$, $-N(CH_3)(CH_2CH_3)$ and $-N(CH_2CH_3)_2$ groups. Aminolysing the surface is convenient as the reagents involved are cheap, chemically stable and non-toxic.

In another example, functionalising the surface of the substrate may comprise exposing the surface to irradiation with UV light, gamma rays or ion beams.

In another example, the surface may be functionalised electrochemically.

The aforementioned functionalisation reactions can provide a variety of surface functional groups on the surface of the substrate such as amine, hydroxyl, alkyloxy, and carboxyl groups. These groups are reactive and can be directly chemically bound to a polymer, as will be discussed in more detail below. For example, most of these groups (and particularly amine, hydroxyl and carboxyl groups) are nucleophilic and therefore can undergo nucleophilic addition reactions or nucleophilic substitution reactions with appropriate reactive moieties on a polymer in order to form a covalent bond to the polymer.

In a preferred embodiment, the surface functional groups comprise a polymerisable moiety, for example an unsaturated bond. Examples of a polymerisable moiety include a carbon-carbon triple bond (C≡C), a carbon-carbon double bond (C═C), a carbon-oxygen double bond (C═O), or a free radical, such as an oxygen radical —O. or a methylene radical —$CH_2$.

The above-described functionalisation processes are capable of producing a surface functional group comprising a polymerisable moiety. For instance, treatment of the substrate with an alcohol plasma or an oxygen plasma can produce carboxyl groups (—COOH or COO⁻), or aldehyde or ketone moieties such as —C(═O)H or —C(═O)$CH_3$, or oxygen radicals —O.

In a preferred embodiment, therefore, step (b) comprises functionalising the surface of the substrate to produce surface functional groups thereon, wherein the surface functional groups comprise a polymerisable moiety. For example, step (b) may comprise treating the surface of the substrate with an oxygen plasma to produce surface functional groups of the substrate surface comprising carboxyl groups, or aldehyde or ketone moieties such as —C(═O)H or —C(═O)$CH_3$.

Two-Stage Functionalisation Step

If a desired surface functional group cannot be produced by a single functionalisation step as described above, the functionalisation step, step (b), may instead comprise two or more stages. A two-stage functionalisation reaction is particularly useful where the desired surface functionalisation group comprises a carbon-carbon unsaturated bond, for example a carbon-carbon double bond (C═C) or a carbon-carbon triple bond (C≡C).

Thus, in some embodiments, functionalising the surface of the substrate comprises
(b)(i) treating the surface to produce reactive groups on the surface; and
(b)(ii) reacting the reactive groups with a surface functional group precursor to produce surface functional groups.

Generally, step (b)(i) of treating the surface to produce reactive groups involves treating the surface using one or more of the one-step functionalisation processes described above. Thus, treating the surface to produce reactive groups may comprise exposing the surface to a plasma. The plasma may typically comprise one or more of oxygen, alcohols, nitrogen, amines and hydrogen. In one embodiment, treating the surface to produce reactive groups comprises exposing the surface to an oxygen plasma. In such cases, the reactive groups may include one or more groups selected from hydroxy, alkyloxy, carboxyl, —O⁻ and —COO⁻. In another embodiment, treating the surface to produce reactive groups comprises exposing the surface to a plasma comprising one or more of nitrogen, ammonia and an amine (preferably methylamine or ethylamine). In such cases, the reactive groups may include one or more groups selected from $-NH_2$, $-NHCH_3$, $-N(CH_3)_2$, $-NHCH_2CH_3$, $-N(CH_3)(CH_2CH_3)$ and $-N(CH_2CH_3)_2$.

Similarly, treating the surface to produce reactive groups may comprise exposing the surface to a reactive chemical species. One example of a reactive chemical species is an oxidant such as a combination of sulphuric acid and a permanganate salt. In such cases the reactive groups may include one or more groups selected hydroxyl and carboxyl groups. Another example of a reactive chemical species is an etching reagent such as sodium hydroxide; in such cases the reactive groups typically include hydroxyl groups.

In a further example of chemical etching, treating the surface to produce reactive groups may comprise aminolysing the surface as described above. In such cases the reactive groups may include one or more of $-NH_2$, $-NHCH_3$, $-N(CH_3)_2$, $-NHCH_2CH_3$, $-N(CH_3)(CH_2CH_3)$ and $-N(CH_2CH_3)_2$ groups.

Surface treatment processes including the above-described examples produce reactive groups on the surface of the substrate. A reactive group is a species which can react with a surface functional group precursor to provide a surface functional group on the surface of the substrate. Accordingly, the nature of the reactive group is not particularly limited: a suitable surface functional group precursor may be selected which reacts with the reactive group to provide a surface functional group precursor.

Treatment of the surface to form reactive groups in step (b)(i) will form a plurality of reactive groups (which may be the same or different) on the substrate surface. Each reactive group within the plurality of reactive groups formed by the treatment step (b)(i) may be the same. For instance, etching of a surface with sodium hydroxide typically produces hydroxyl groups. However, more commonly, the plurality of reactive groups produced by the functionalisation step, (b), may comprise two or more different kinds of reactive group. This is commonly the case where the surface treatment step (b)(i) involves treatment of the surface of the substrate with a plasma.

It is also possibly to produce two or more different kinds of reactive groups on the surface of the substrate by performing two or more surface treatment steps (b)(i) before providing the polymeric layer.

As the reactive group must be able to react with another chemical species, it usually comprises a chemically reactive moiety. For example, a reactive group may comprise one or more of a radical, an anion, an electrophile or a nucleophile. Where the reactive group comprises a radical moiety, the reactive group may for instance comprise or consist of an —O. group, an —S. group, a —$CH_2$. group, a —$CHCH_3$. group, or a —$C(CH_3)_2$. group. Where the reactive group comprises an anion, it may for instance comprise or consist of an —O⁻ group or a —COO⁻ group. Where the reactive group comprises a nucleophile, it may for instance comprise or consist of —OH, —COOH, —OR, —COOR, —SH, —SR, and —NR$_2$.

The reactive groups are typically capable of acting as nucleophiles. Typically, therefore, the reactive groups comprise one or more of —OR, —O$^-$, —COO$^-$, —COOR and —NR$_2$. Preferably, the reactive groups comprise one or more of —OH, —O$^-$, —COO$^-$, —COOH and —NR$_2$. Exemplary reactive groups include —OH, —COOH and —NH$_2$.

Each R may be independently selected from H, or $C_{1-6}$ alkyl, $C_{2-6}$ alkenyl or $C_{2-6}$ alkynyl. Preferably, each R is independently selected from H and $C_{1-4}$ alkyl. Most preferably, each R is H.

Any R group capable of substitution may optionally be substituted by one or more substituents. For instance, R may be substituted by 0, 1 or 2 substituents selected from hydroxy, $C_{1-4}$ alkyl, $C_{1-4}$ alkoxy, —COOR' and —NR'$_2$. Preferably, R is unsubstituted.

Where present, each R' is independently selected from H and $C_{1-4}$ alkyl.

The reactive groups include a linker $L_1$ which is a divalent moiety which is covalently bound to the substrate and to one of the aforementioned nucleophiles (e.g. —OH, —O$^-$, —COO$^-$, —COOH or —NR$_2$). The linker $L_1$ thus covalently binds the chemically reactive nucleophilic group to the substrate via one or more intervening atoms. The linker $L_1$ comprises a covalent bond and may also comprise one or more of O, S, N, and C. For example, $L_1$ may comprise one or more of a covalent bond, —O—, —NR'— and —CR'$_2$— wherein each R' is as defined above. In a preferred embodiment, $L_1$ consists of one or more groups each independently selected from a covalent bond, —O—, —NR'— and —CR'$_2$—. Typically, $L_1$ comprises one or more of —O—, —NH— and —CH$_2$—. By "one or more of" is meant that a linker $L_1$ may contain several of the aforementioned groups. For instance, $L_1$ may comprise 1 to 20 groups or 1 to 10 groups each independently selected from —O—, —NR'— and —CR'$_2$—; preferably 1 to 10 groups each independently selected from —O—, —NH— and —CH$_2$—. Preferred examples of $L_1$ include a covalent bond, —O—, —NH— and —CH$_2$—. In an example, $L_1$ is a covalent bond. In another example, $L_1$ is —NH—(CH$_2$)$_2$—O—(CH$_2$)$_2$—O—(CH$_2$)$_2$—.

In a preferred embodiment, therefore, the reactive groups are selected from one or more of —OH, —O$^-$, —COO$^-$, —COOH and —NR$_2$, wherein each R is independently selected from H and unsubstituted $C_{1-4}$ alkyl.

The reactive groups produced in step (b)(i) are reacted with a surface functional group precursor in step (b)(ii) to produce surface functional groups. A surface functional group precursor is a group which can react with a reactive group to produce a surface functional group.

As the surface functional group precursor must be able to react with the reactive groups, which are typically nucleophilic, the surface functional group precursor is generally susceptible to reaction with a nucleophile. Typically the surface functional group precursor can undergo an addition or substitution reaction with a nucleophilic reactive group. Usually, therefore, a surface functional group precursor is electrophilic.

In some embodiments, the surface functional group precursor can undergo a nucleophilic substitution reaction with a reactive group. In such embodiments, the surface functional group typically comprises a leaving group. Examples of leaving groups include carboxylate moieties and halogen atoms (F, Cl, Br and I) which can leave as halide ions (F$^-$, Cl$^-$, Br$^-$ and I$^-$). Cl$^-$ is a particularly preferred leaving group.

In some embodiments, the surface functional group precursor can undergo a nucleophilic addition reaction with a reactive group. In such embodiments, the surface functional group precursor typically comprises an electrophilic double bond. For example, the surface functional group precursor may comprise a carbonyl group (—C(=O)—) or a conjugated carbonyl group (—C=C—C(=O)—).

The surface functional group precursor is reacted with the reactive groups in order to add a desired surface functional group to the surface of the substrate. In preferred embodiments, it is desired to add a polymerisable moiety to the surface of the substrate in order to be available for inclusion in the polymeric layer. Preferably, therefore the surface functional group precursor comprises a polymerisable moiety. A polymerisable moiety is typically a moiety comprising an unsaturated bond. Preferably, therefore, the surface functional group precursor comprises one or more of a carbon-carbon triple bond (C≡C), a carbon-carbon double bond (C=C), or a carbon-oxygen double bond (C=O). For instance, the surface functional group precursor may comprise an alkenyl group, an alkynyl group, or a carbonyl group.

In one preferred embodiment, the surface functional group precursor is a species which can undergo a nucleophilic substitution reaction in order to yield a surface functional group comprising a polymerisable moiety. In such an embodiment, the surface functional group precursor typically comprises an unsaturated bond and a leaving group. For example, the surface functional group may comprise a carbon-carbon double bond and a halogen atom.

Particularly preferably, the surface functional group precursor is a compound of formula R$_2$C=CR—C(=O)-Hal, wherein R is as described herein and may be optionally substituted as described herein; and Hal is a halogen, preferably Cl. In another particularly preferred example, the surface functional group precursor is a compound of formula R$_2$C=CR—C(=O)—O—C(=O)—CR=CR$_2$ wherein R is as described herein and may be optionally substituted as described herein.

Most preferably, the surface functional group precursor is selected from methacryloyl chloride, acryloyl chloride, methacryloyl anhydride and acryloyl anhydride. The latter surface functional group precursors are also known as methacrylic anhydride and acrylic anhydride.

Described above are a one-stage functionalisation process and a two-stage functionalisation process. As the skilled person will appreciate, it would of course be possible to repeat one or more of these stages. This may be useful in forming a higher density of surface functional groups, or a greater variety of surface functional groups. Accordingly, step (b) may be performed more than once. Similarly, where steps (b)(i) and (b)(ii) are performed, one or both of those steps may be performed more than once. Further steps (b)(i) and (ii) may be performed in any order. For instance, step (b)(i) may be repeated before step (b)(ii) is performed; or steps (b)(i) and (b)(ii) may be performed and then subsequently steps (b)(i) and (b)(ii) may be performed again. However, step (b) (including steps (b)(i) and (b)(ii) where performed) are performed before step (c).

Surface Functional Groups

The functionalisation step, (b), produces surface functional groups on the surface of the substrate. The functionalisation process will form a plurality of surface functional groups, typically a very large number of surface functional groups. The large number of surface functional groups is advantageous as it provides a large number of sites at which the polymer may be chemically bound to the substrate.

Each surface functional group within the plurality of surface functional groups formed by the functionalisation step (b) may be the same. For instance, etching of a surface with sodium hydroxide typically produces hydroxyl groups. However, more commonly, the plurality of surface functional groups produced by the functionalisation step, (b), may comprise two or more different kinds of surface functional group. This is commonly the case where the functionalisation step involves treatment of the surface of the substrate with plasma.

It is also possibly to produce two or more different kinds of surface functional groups on the surface of the substrate by performing two or more functionalisation steps before providing the polymeric layer.

A surface functional group is group which is capable of forming a chemical bond to the polymeric layer. Herein, the term "chemical bond" is intended to refer to a covalent bond or an ionic bond. The preferred form of chemical bond is a covalent bond. Accordingly, a surface functional group is preferably a group which is capable of forming a covalent bond to the polymeric layer.

The surface functional group may form a covalent bond to the polymer by a wide variety of mechanisms. In some cases, the surface functional groups may form a covalent bond to a pre-formed polymer. For example, a pre-formed polymer may be placed in contact with the surface of the substrate having surface functional groups thereon.

In order to form a covalent bond to the polymer, the surface functional group may act as a nucleophile and form a covalent bond with electrophilic moieties on the polymer by a nucleophilic addition or a nucleophilic substitution reaction. For example, where the polymer comprises carboxyl groups, and the surface functional groups include one or more of hydroxy, —O$^-$, —COOH or —COO$^-$ then the surface functional groups may undergo an esterification reaction with the polymer. Similarly, where the polymer comprises carboxyl groups, and the surface functional groups include amine species such as —NH$_2$, then the surface functional groups may undergo an amide condensation reaction with the polymer.

In some embodiments, therefore, the surface functional group comprises a nucleophilic group. For instance, the surface functional group may comprise or consist of —OH, —COOH, —OR, —COOR, —SH, —SR, and —NR$_2$. For example, where the surface functional group is a nucleophilic group, it may preferably comprise —OR, —O$^-$, —COO$^-$, —COOR and —NR$_2$; more preferably it may comprise —OH, —O$^-$, —COO$^-$, —COOH and —NR$_2$; and most preferably it may comprise —OH, —COOH and —NH$_2$. R is as defined above and may be optionally substituted as described above.

The aforementioned nucleophilic surface functional groups are attached to the surface of the substrate by a linker -L$_1$- as described above.

In some embodiments, therefore, where the surface functional groups are nucleophilic, the surface functional groups are selected from one or more of —OH, —O$^-$, —COO$^-$, —COOH and —NR$_2$, wherein each R is independently selected from H and unsubstituted C$_{1-4}$ alkyl.

More preferably, the surface functional groups are capable of incorporation into the polymeric layer by co-polymerisation. Where the surface functional groups comprise a polymerisable moiety, they can be co-polymerised with a polymer precursor to form the polymeric layer. This is a very convenient method of generating the polymeric layer, as will be discussed below. Accordingly, in a preferred embodiment, the surface functional groups comprise a polymerisable moiety. As explained above, a polymerisable moiety is typically a moiety comprising an unsaturated bond. Preferably, therefore, the surface functional groups comprise one or more of a carbon-carbon triple bond (C≡C), a carbon-carbon double bond (C═C), or a carbon-oxygen double bond (C═O). For instance, the surface functional groups may comprise an alkenyl group, an alkynyl group, or a carbonyl group. Most preferably, the surface functional groups comprise a carbon-carbon double bond (C═C).

The surface functional groups may therefore comprise a moiety derived from the reactive group and a polymerisable moiety. For example, the surface functional groups may be groups of formula -L$_1$-X-L$_2$-CR═CR$_2$, -L$_1$-X-L$_2$-C≡CR, or -L$_1$-X-L$_2$-C(═O)R.

X is O or NR.

R is as described herein. Thus, each R is independently selected from H, or C$_{1-6}$ alkyl, C$_{2-6}$ alkenyl or C$_{2-6}$ alkynyl, which may be optionally substituted as described above. Preferably R is unsubstituted.

L$_1$ is a linker as defined above. Thus, L$_1$ is preferably a linker consisting of one or more groups each independently selected from a covalent bond, —O—, —NR'— and —CR'$_2$—, wherein R' is H or C$_{1-4}$ alkyl.

L$_2$ is a linker selected from a covalent bond, or a carbonyl group, or C$_{1-6}$ alkylene, C$_{2-6}$ alkenylene or C$_{2-6}$ alkynylene which may be optionally substituted. Preferably, L$_2$ is selected from a covalent bond, a carbonyl group, a C$_{1-4}$ alkylene and a C$_{2-4}$ alkenylene. More preferably, L$_2$ is selected from a carbonyl group and a C$_{1-2}$ alkylene. Most preferably, L$_2$ is a carbonyl group.

L$_2$ may be optionally substituted at any position capable of substitution. For example, L$_2$ may be substituted by 0, 1, or 2 substituents. Typically, L$_2$ is substituted by 0 or 1 substituents. The substituents upon L$_2$, where present, are typically each independently selected from hydroxy, oxo, halogen, C$_{1-4}$ alkyl, C$_{2-4}$ alkenyl, —COR', —CO$_2$R', and —NR'$_2$. Most preferably, however, L$_2$ is unsubstituted.

In a preferred embodiment, therefore, the surface functional groups are groups of formula -L$_1$-X-L$_2$-CR═CR$_2$, -L$_1$-X-L$_2$-C≡CR, or -L$_1$-X-L$_2$-C(═O)R wherein X is O or NR; R is H or C$_{1-4}$ alkyl; L$_1$ is a covalent bond or —NH—(CH$_2$)$_2$—O—(CH$_2$)$_2$—O—(CH$_2$)$_2$—; and L$_2$ is a carbonyl group.

In a particularly preferred embodiment, the surface functional groups are groups of formula -L$_1$-X-L$_2$-CR═CR$_2$, wherein X is O or NR; R is H or C$_{1-4}$ alkyl; L$_1$ is a covalent bond or —NH—(CH$_2$)$_2$—O—(CH$_2$)$_2$—O—(CH$_2$)$_2$—; and L$_2$ is a carbonyl group.

Polymeric Layer

The method of producing an optical component comprises a step (c) which involves providing a polymeric layer chemically bound to the surface functional groups.

As the skilled reader will appreciated, the surface functional groups are of course changed by chemical binding to the polymer. Accordingly, once step (c) of the method has been performed and the surface functional groups have become chemically bound to the polymeric layer, they will no longer correspond exactly to the chemical moieties produced by the functionalisation step(s) and described in the preceding section.

In some embodiments, providing a polymeric layer comprising a polymer chemically bound to the surface functional groups involves providing a polymer (i.e. a pre-formed polymer) and then reacting it with the surface functional groups.

In a preferred embodiment, however, the polymer is formed in situ on the substrate. Preferably, therefore, the step of providing a polymeric layer comprises disposing a layer comprising a polymer precursor on the surface of the substrate and then polymerising the polymer precursor. The surface of the substrate is the surface having surface functional groups thereon, and so the layer comprising the polymer precursor, and subsequently the polymer, will contact the surface functional groups on the surface.

Polymerisation may be initiated by any conventional method, for example by applying heat or UV light. In some cases, polymerisation may also comprise leaving the polymer precursor to cure.

In an exemplary method, therefore, step (c) involves providing a solution comprising a polymer precursor; disposing the solution comprising the polymer precursor in contact with the surface functional groups; and polymerising the polymer precursor to provide a polymeric layer comprising a polymer.

It is preferred to form the polymer is formed in situ on the substrate from a polymer precursor, because the polymer precursor can be easily manipulated into a desired shape (for instance, into a desired thickness). For example, the polymer precursor may be manipulated into the desired shape of the eventual polymeric layer. By way of example, the polymer precursor may be disposed in the form of a layer of a desired thickness prior to polymerisation. For instance, step (c) may involve providing a solution comprising a polymer precursor; disposing a layer of the solution comprising the polymer precursor on the surface of the substrate; and polymerising the polymer precursor to provide a polymeric layer comprising a polymer.

A particular advantage of forming the polymeric layer in situ on the substrate from a polymer precursor is that the polymer precursor may be used to provide a layer of polymer precursor (and hence a polymeric layer, after polymerisation) of uniform thickness. The thickness of a layer may be defined as the mean extent of that layer in a direction perpendicular to the surface of the substrate, measured from the surface of the substrate. Where a layer has a uniform thickness, there may be minor variations in thickness between differing points in the layer on the surface of the substrate. However, where a layer has uniform thickness, the thickness of the said layer typically varies by less than 10% from the mean thickness preferably by less than 5% from the mean thickness, most preferably by less than 1% from the mean thickness.

Preferably, therefore, step (c) involves disposing a layer comprising a polymer precursor on the surface of the substrate, wherein the said layer has a uniform thickness, and polymerising the polymer precursor to provide a polymeric layer comprising a polymer.

It is possible to achieve a layer having a uniform thickness in a variety of ways. For example where the layer comprising a polymer precursor is a flowable medium, it will tend to form a layer of uniform thickness under the influence of gravity alone. Accordingly, in some embodiments step (c) involves providing a solution comprising a polymer precursor; disposing a layer of the solution comprising the polymer precursor on the surface of the substrate, wherein the layer has uniform thickness; and polymerising the polymer precursor to provide a polymeric layer of uniform thickness comprising a polymer.

More preferably, if the layer comprising the polymer precursor is not easily flowable (e.g. gelatinous), an active step(s) may be needed to provide a layer of uniform thickness comprising the polymer precursor. For instance, the layer comprising the polymer precursor may be manually spread over the surface to a uniform thickness. In a particularly preferred embodiment the layer comprising the polymer precursor is disposed on the substrate by spin-coating; this process provides layers of low thickness having excellent uniformity.

Thus, in a particularly preferred embodiment, the step of providing a polymeric layer comprises disposing a layer comprising a polymer precursor on the surface of the substrate by spin-coating, and then polymerising the polymer precursor.

Where the polymer is formed in situ from a polymer precursor as described above, the polymer may be allowed to react with surface functional groups during and/or after the polymerisation step, in order to chemically bind the polymer to the surface functional groups. Preferably, however, the surface functional groups are chemically bound to the polymer by co-polymerisation. That is, where the polymerisation step involves co-polymerising the surface functional groups and a polymer precursor, the surface functional groups are incorporated into the polymer by chemical bonds.

In a preferred embodiment, therefore, in the step of providing a polymeric layer comprising a polymer chemically bound to the surface functional groups, a polymer precursor is copolymerised with the surface functional groups. In such embodiments, the surface functional groups comprise a polymerisable moiety.

In an exemplary method, therefore, step (c) involves disposing a layer comprising a polymer precursor on the surface of the substrate (preferably by spin-coating), and copolymerising the polymer precursor and the surface functional groups to provide a polymeric layer comprising a polymer chemically bound to the surface functional groups. For example, step (c) may involve providing a solution comprising a polymer precursor; disposing a layer of the solution comprising the polymer precursor on the substrate in contact with the surface functional groups; and copolymerising the polymer precursor and the surface functional groups to provide a polymeric layer comprising a polymer chemically bound to the surface functional groups.

An example of a process for producing an optical component using a two-stage functionalisation step, followed by copolymerisation of the surface functional groups with a polymer precursor, is illustrated in FIG. 1. In the embodiment illustrated in FIG. 1, a substrate is provided in step (a). A reactive group of formula —XH is produced on the surface of the substrate in step (b)(i). X is O or NR. In step (b)(ii), the reactive group —XH is reacted with a surface functional group precursor to produce a surface functional group of formula -$L_1$-X-$L_2$-CR=$CH_2$ wherein $L_1$ is a covalent bond, and $L_2$ is a carbonyl group. Subsequently, in step (c), the terminal C=$CH_2$ moieties of the surface functional groups are co-polymerised with a polymer precursor which is a hydrogel monomer to produce a polymeric layer comprising a hydrogel polymer covalently bound to the surface functional groups.

The thickness of the polymeric layer is not particularly limited. However, it is desirable to ensure that the polymeric layer is not too thick; if the layer is very thick, it may have optical transmission properties and further may act as a reservoir for analyte, meaning that a sensor formed from an optical component according to the invention may have a very long response time. Accordingly, generally the thickness of the polymeric layer is less than about 1000 μm. Preferably, the thickness of the polymeric layer is less than about 500 μm; more preferably, the thickness of the polymeric layer is about 100 μm or less.

It is also desirable to ensure that the polymeric layer is not too thin. Where the polymeric layer is very thin, the amount of luminescent compound immobilised therein may be extremely small and the total optical signal produced by the luminescent compound immobilised in the polymeric matrix may be undesirably weak. Accordingly, generally the polymeric layer has a thickness of at least about 0.1 μm. Preferably, the polymeric layer has a thickness of at least about 1 μm. More preferably, the polymeric layer has a thickness of at least 10 μm.

In a preferred embodiment, the polymeric layer has a thickness of from about 1 to about 200 μm, preferably from about 10 to about 100 μm. For example, the polymeric layer may have a thickness of about 20 μm, or about 30 μm, or about 40 μm.

Polymer and Polymer Precursor

In preferred embodiments, the polymeric layer is formed by polymerisation of a polymer precursor as described above. The polymer precursor is a chemical compound which can be polymerised to form a polymeric layer. The polymer precursor can be copolymerised with other polymerisable species such as a polymerisable moieties of the surface functional groups.

The polymer precursor comprises a polymerisable moiety. For instance, the polymer precursor is typically an unsaturated monomer. Preferably, the polymer precursor comprises a C=C moiety and/or a C=O moiety.

The polymer precursor may be hydrophilic or hydrophobic. In some embodiments, the polymer precursor is a hydrophilic monomer. In a preferred embodiment, the polymer precursor is a hydrogel monomer. A hydrogel monomer is a hydrogel precursor; i.e. a species which, when polymerised, forms a hydrogel. In particular examples, the polymer precursor is an acrylamide-based monomer, i.e. a derivative of acrylamide. Thus, particular examples of the polymer precursor are dimethyl acrylamide and (hydroxyethyl)methacrylate ("HEMA").

One or more types of polymer precursor may be used.

The polymer itself may be selected from a wide variety of known polymers which are suitable for optical sensing applications. The polymer is typically gas-permeable, and may also be liquid-permeable. Generally, the polymer is hydrophilic. A particularly suitable polymer is a hydrogel.

Where the polymeric layer is formed by polymerisation of a polymer precursor, optionally together with other components such as a luminescent compound precursor and/or surface functional groups, a cross-linker may be added. Thus, the layer comprising a polymer precursor may also comprise a cross-linker. Preferred cross-linkers include acrylamide-based cross-linkers and acrylate-based cross-linkers. Thus, particular examples of a cross-linker are methylene bisacrylamide and PEG-dimethacrylates. However, the cross-linker is not always necessary. Similarly, a polymerisation initiator may be added. Thus, the layer comprising a polymer precursor may also comprise a polymerisation initiator. Examples of a polymerisation initiator which may be present include azoiniators (such as AIBN, azobisisobutyronitrile) and benzoyl peroxide. However, a polymerisation initiator is not always necessary; polymerisation may be initiated by other common means such as irradiation with UV light, or heating.

Luminescent Compound

The polymeric layer comprises a luminescent compound immobilised in the polymeric layer. As used herein, a luminescent compound is a compound having at least one optical property which varies upon interaction with an analyte.

An optical property of a luminescent compound may be the luminescence emission intensity (such as the fluorescence emission intensity or the phosphorescence emission intensity). Another optical property of a luminescent compound may be the absorption strength. Yet another optical property of a luminescent compound may be the wavelength of maximum luminescence emission intensity (such as the wavelength of peak fluorescence emission intensity or the wavelength of peak phosphorescence emission intensity). Yet another optical property of a luminescent compound may be the wavelength of maximum absorption strength. Yet another optical property of a luminescent compound may be its luminescence lifetime (such as the fluorescence lifetime or the phosphorescence lifetime).

One or more of the aforementioned optical properties of the luminescent compound may vary when the luminescent compound interacts with an analyte. Thus, one or more optical properties of the luminescent compound may be detected (for instance, may be monitored over time), and variation in said optical property indicates a change in the level of the relevant analyte.

It is preferred that the luminescent compound has an optical emission property which varies when the luminescent compound interacts with an analyte. In applications where the amount of luminescent compound is small, it can be difficult to detect the absorption against the background of excitation light. It is therefore preferred that the luminescent compound has a luminescent emission spectrum which varies when the luminescent compound interacts with analyte.

The luminescent emission spectrum may be a fluorescence emission spectrum or a phosphorescence emission spectrum. However, a phosphorescence emission spectrum is typically weaker than a fluorescence emission spectrum as it involves a spin-forbidden transition. In order to provide an optical component with a strong optical response to excitation light, it is therefore preferred that the luminescent compound has a fluorescence emission spectrum which varies when the luminescent compound interacts with an analyte.

Accordingly, it is preferred that the luminescent compound comprises a fluorophore. A fluorophore is a moiety which can absorb light and re-emit light by fluorescent emission. Usually, the fluorophore absorbs light in the visible region of the electromagnetic spectrum. The fluorophore also usually emits light in the visible region of the electromagnetic spectrum. By "the visible region of the electromagnetic spectrum" is meant electromagnetic radiation having a wavelength of from about 400 nm to about 700 nm. The fluorophore may also absorb and/or emit radiation outside the visible region of the electromagnetic spectrum.

In a preferred embodiment, therefore, the luminescent compound comprises a fluorophore, and the fluorescence emission spectrum of the fluorophore varies in the presence of an analyte.

Variation in an optical property of the luminescent compound (such as the emission spectrum of the luminescent compound) is induced by interaction with an analyte. Possible modes of interaction between the analyte and the luminescent compound include:

protonation of the luminescent compound;
deprotonation of the luminescent compound;

collisional quenching of an excited state of the luminescent compound;

photoinduced electron transfer; and binding to a lone pair of electrons of the luminescent compound.

Other modes of interaction are possible. These interactions will alter the one or more optical properties of the luminescent compound, which may be optically detected.

In some cases, as where the interaction between analyte and luminescent compound involves collisional quenching of the luminescent compound, the analyte does not bind to the luminescent compound. However, in other cases, a chemical bond such as an ionic bond, a non-covalent bond (such as a hydrogen bond or a CH-n interaction) or a covalent bond may be formed between the analyte and the luminescent compound. In such cases, the luminescent compound may comprise a receptor moiety. A receptor moiety is a moiety which can bind to an analyte. It may be preferred that the luminescent compound comprises a receptor moiety, as a receptor moiety typically binds preferentially to the analyte and not to other chemical species. Thus, a luminescent compound comprising a receptor moiety typically generates an optical signal associated specifically with the analyte, which has low susceptibility to interference from other species.

Any luminescent compound may be used. A number of examples are provided below for illustrative purposes only.

In one example, the luminescent compound may comprise a moiety of formula (I):

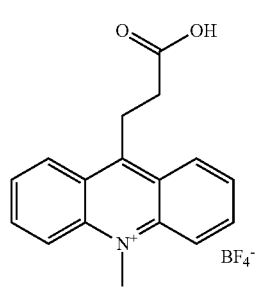

(I)

Or a derivative thereof. See Julian et al., "Fibre optic chloride sensor based on fluorescence quenching of an acridinium dye", 20th international conference on optical fibre sensors, 2009:7503:750314 and Lin et al., Organic Letters, 2009:11:4858-4861. The compound of formula (I) does not comprise a receptor moiety; however, it is susceptible to collisional quenching in the presence of Cl[−]. Collisional quenching with Cl[−] decreases the fluorescence lifetime of a species of formula (I) and reduces the intensity of its fluorescence Thus, where the luminescent compound comprises a compound of formula (I), the luminescent compound is useful for detecting the presence of chloride ions by detecting or monitoring the fluorescence intensity or fluorescence lifetime of the luminescent compound.

In another example, the luminescent compound may comprise a moiety of formula (II):

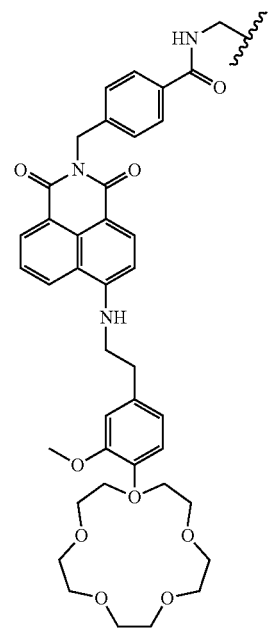

(II)

Or a derivative thereof. The wavy line indicates the point of attachment to another moiety; this may be, for example, the polymer of the polymeric layer or an organic moiety such as an alkyl group. The species of formula (II) comprises both a receptor (the cryptand, which can bind Na[+]) and a fluorophore comprising the polycyclic aryl moiety. When Na[+] binds to the cryptand, the fluorescent emission of this moiety alters.

In another example, the luminescent compound may comprise a moiety of formula (III):

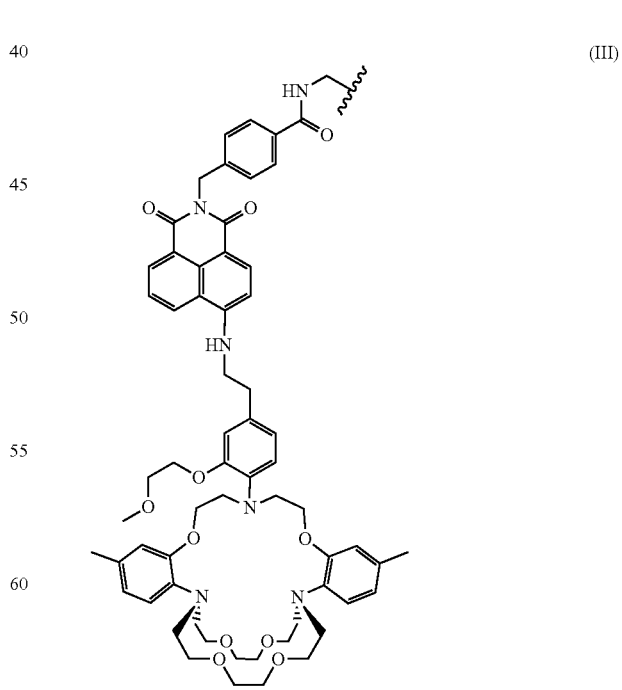

(III)

Or a derivative thereof. The wavy line indicates the point of attachment to another moiety; this may be, for example, the polymer of the polymeric layer or an organic moiety such as an alkyl group. The species of formula (III) comprises both a receptor (the cryptand, which can bind K⁺) and a fluorophore comprising the polycyclic aryl moiety. When K⁺ binds to the cryptand, the fluorescent emission of this moiety alters.

In another example, the luminescent compound may comprise a moiety of formula (IV):

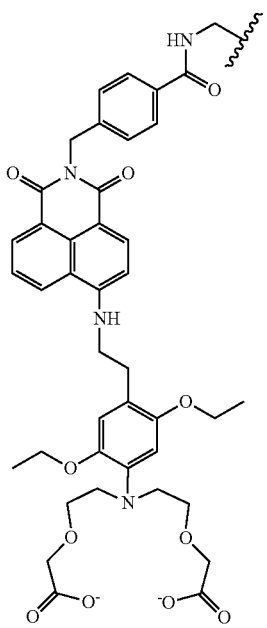

(IV)

Or a derivative thereof. See, for instance, Tusa & He, J. Mater. Chem., 2005:15:2640-2647; de Silva et al., Org. Biomol. Chem., 2008:6:2468-2481. The wavy line indicates the point of attachment to another moiety; this may be, for example, the polymer of the polymeric layer or an organic moiety such as an alkyl group. The species of formula (IV) comprises both a receptor (the moiety including the pair of carboxylate ions which can bind $Ca^{2+}$) and a fluorophore comprising the polycyclic aryl moiety. When $Ca^{2+}$ binds to the receptor, the fluorescent emission of this moiety alters.

In another example, the luminescent compound may comprise a moiety of formula (V) or (VI):

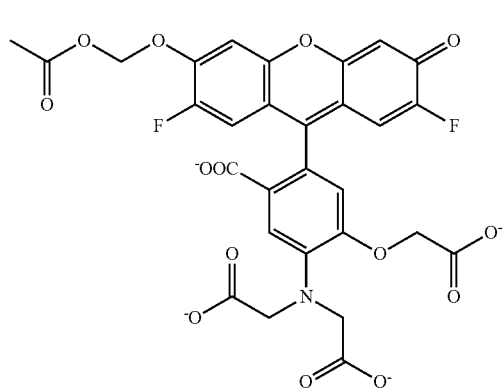

(V)

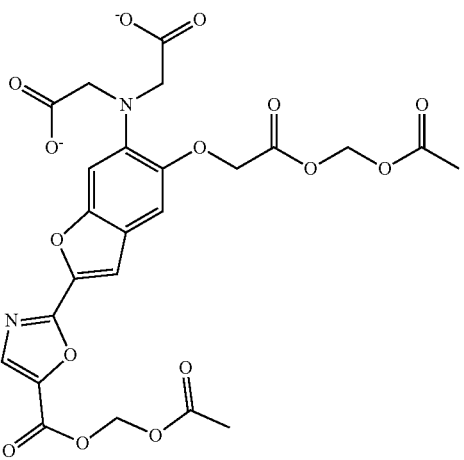

(VI)

Or a derivative thereof. See, for instance, Lee et al., Anal. Chem., 2009:81:538 or Martinez-Zaguila et al., Cell Physiol. Biochem., 1998:8:158. The moiety of formula (V) or (VI) may be attached at any point to the polymer comprised in the polymeric layer. These compounds are known as Mag-fluo-4 (compound (V)) and Mag-fura-2 (compound (VI)) respectively. The species of formula (V) and (VI) bind to $Mg^{2+}$ ions via the methyl ester moieties. Compound (VI) is therefore an example of a luminescent compound comprising more than one receptor. These compounds also comprise a fluorophore comprising a polycyclic aryl moiety. When $Mg^{2+}$ binds to either of these compounds, their fluorescent emission alters.

In another example, the luminescent compound may comprise a moiety of formula (VII) or (VIII):

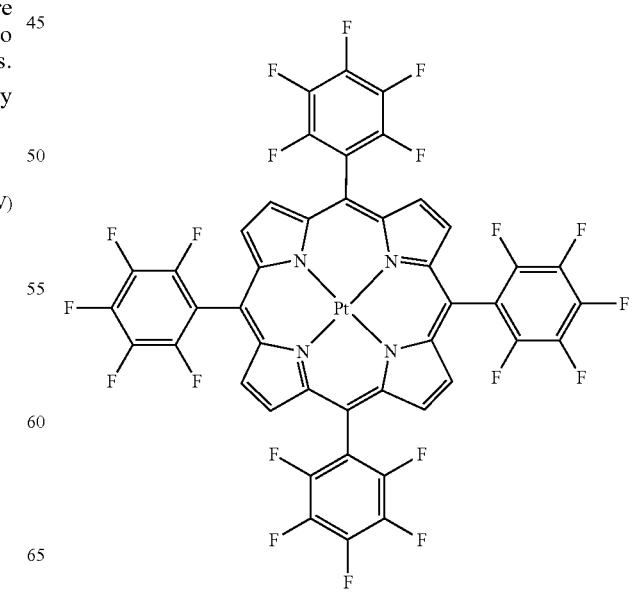

(VII)

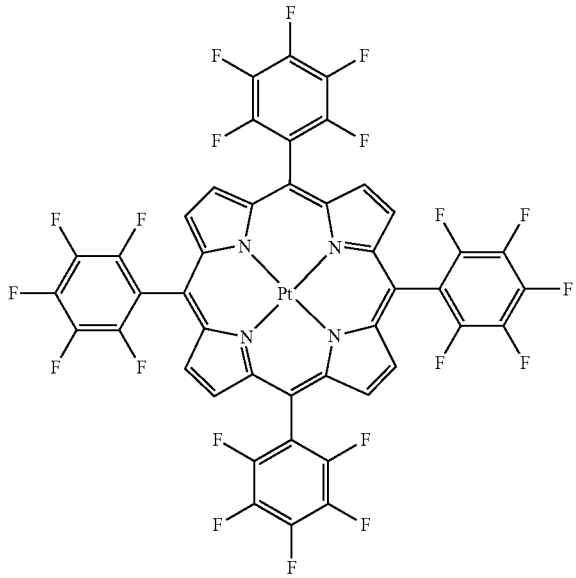

(VIII)

Or a derivative thereof. See, for instance, Cua & Lob, Sensors and Actuators B, 2011:1555:53-57 or Escebedo et al., Anal. Chem., 2017:89:1697-1703. The species of formula (VII) and (VIII) do not comprise receptor moieties; however, they are susceptible to collisional quenching in the presence of $O_2$. Collisional quenching with $O_2$ decreases the fluorescence lifetime of the species of formula (VII) or (VIII). Thus, where the luminescent compound comprises a formula (VII) or (VIII), the luminescent compound is useful for detecting the presence of oxygen by detecting or monitoring the fluorescence lifetime of the luminescent compound.

In another example, the luminescent compound may comprise a moiety of formula (IX):

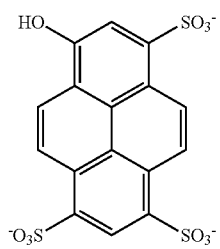

(IX)

That is, pyranine, or a derivative thereof. See for instance Ge et al., "High-stability non-invasive autoclavable naked optical CO2 sensor", Biosensors and Bioelectronics, 2003: 18:857-865. This moiety may be attached at any point except the hydroxyl group to the polymer of the polymeric layer. The compound of formula (IX) does not comprise a separate receptor and fluorophore; the fluorophore itself acts as the receptor. The moiety of formula (IX) can be used to detect acid or $CO_2$, because $CO_2$ forms an acid (carbonic acid) in the presence of water. In the presence of acid (such as carbonic acid formed by $CO_2$), the hydroxyl group of the moiety of formula (IX) is protonated. However, as the concentration of acid or $CO_2$ decreases, the hydroxyl moiety becomes deprotonated, leaving a negative charge which is delocalised throughout the fluorophore, changing the fluorescence emission spectrum, and the fluorescence absorption spectrum, of the compound. This change is particularly promoted where the luminescent compound comprising a moiety of formula (IX) is immobilised in the polymeric matrix together with a phase transfer agent. An exemplary phase transfer agent is hexadecyltrimethylammonium hydroxide.

A suitable derivative of pyranine which may be used is a moiety of formula (X), below.

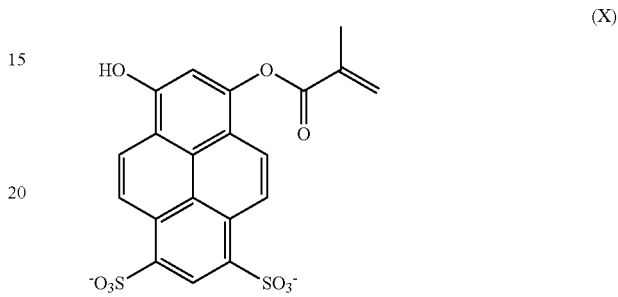

(X)

See for instance Ge et al., "Study on low-cost calibration-free pH sensing with disposable optical sensors", Analytica Chimica Acta, 2012:734:79-87.

In another example, the luminescent compound may comprise a moiety of formula (XI):

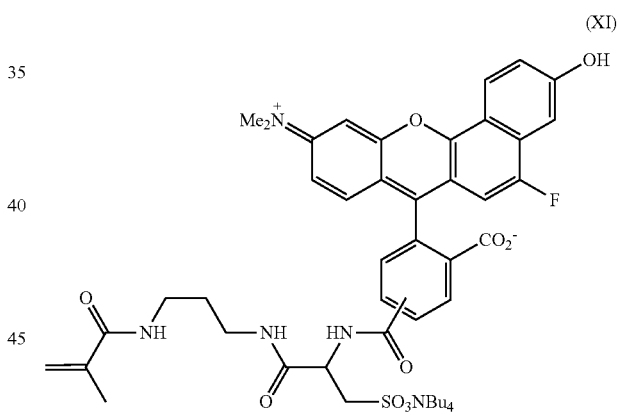

(XI)

Or a derivative thereof. This moiety may be attached at any point to the polymer of the polymeric layer. The compound of formula (XI) behaves in a similar way to the moieties of formula (IX) and (X): it does not comprise a separate receptor and fluorophore; the fluorophore itself acts as the receptor. In the presence of acid, the hydroxyl group of the moiety of formula (XI) is protonated. However, as the concentration of acid decreases, the hydroxyl moiety becomes deprotonated, leaving a negative charge which is delocalised throughout the fluorophore, changing the fluorescence emission spectrum, and the fluorescence absorption spectrum, of the compound.

Other luminescent compounds are known, and in many cases are commercially available; these compounds may also be used as a luminescent compound.

It will be clear from the above that the optical component produced by the process of the invention may be used for the optical sensing of a wide variety of analytes. The analyte may be, for example, an ion, a gas, an inorganic compound or an organic compound. Where the analyte is an organic compound, it is typically a small organic compound, for example an organic compound comprising fewer than 20 carbon atoms. Particular examples of small organic compounds include saccharides, sugar alcohols, and metabolites such as urea or ketones. Particularly preferred examples of the analyte are $Na^+$, $K^+$, $Ca^{2+}$, $Mg^{2+}$, $O_2$, $CO_2$, acid ($H^+$), and $Cl^-$.

Immobilisation of Luminescent Compound

The process for producing an optical component produces a polymeric layer wherein the luminescent compound is immobilised in the polymeric layer. The luminescent compound may be immobilised in the polymeric layer by any suitable means.

Typically, the luminescent compound is suspended in the polymeric layer. In some embodiments, therefore, step (c) comprises suspending a luminescent compound in the polymeric layer.

The luminescent compound may be suspended in the polymeric layer after the polymeric layer has been formed. For example, after providing a polymeric layer comprising a polymer chemically bound to the surface functional groups, step (c) may comprise subsequently suspending a luminescent compound in the polymeric layer. Suspension of a luminescent compound in the polymeric layer can be achieved by dissolving the luminescent compound in a solvent to produce a solution and treating the polymeric layer with the said solution. The process may further comprise drying the polymeric layer to remove some or all of the solvent.

The luminescent compound may alternatively be suspended in the polymeric layer on formation of the polymeric layer. As explained above, in a preferred embodiment, the polymeric layer is prepared by disposing a layer comprising a polymer precursor on the surface of the substrate, and polymerising the polymer precursor to provide a polymeric layer comprising a polymer. The luminescent compound may be provided within the layer comprising the polymer precursor and hence is immobilised in the polymeric layer as it is formed.

For example, step (c) may comprise providing a polymeric layer comprising a polymer chemically bound to the surface functional groups, wherein a luminescent compound is immobilised within the polymeric layer, by disposing a layer comprising a polymer precursor and a luminescent compound on the surface of the substrate, and polymerising the polymer precursor.

Alternatively, the luminescent compound may be chemically bound to the polymeric layer in order to immobilise the luminescent compound. The luminescent compound may be chemically bound to the polymer by an ionic bond or a covalent bond, preferably by a covalent bond.

The luminescent compound may be chemically bound to the polymer in the polymeric layer after the polymeric layer has been formed. For example, after providing a polymeric layer comprising a polymer chemically bound to the surface functional groups, step (c) may comprise subsequently reacting the polymer with a luminescent compound predecessor to produce a luminescent compound chemically bound to the polymer. A luminescent compound predecessor is a compound which can be reacted with the polymer to produce a luminescent compound chemically bound (preferably covalently bound) to the polymer.

The skilled person is able to devise a convenient luminescent compound predecessor and reaction scheme in order to chemically bind a luminescent compound to the polymer using their basic chemical knowledge. For instance, where the polymer comprises nucleophilic groups (such as hydroxyl groups or amine groups), these may be employed to act as nucleophiles in a nucleophilic addition or substitution reaction with the luminescent compound predecessor. By way of example, where the polymer comprises hydroxyl groups or amine groups, the hydroxyl groups may be used to undergo an esterification or amide condensation with a carboxyl group of the luminescent compound precursor.

The luminescent compound may alternatively be chemically bound to the polymeric layer on formation of the polymeric layer. As explained above, in a preferred embodiment, the polymeric layer is prepared by disposing a layer comprising a polymer precursor on the surface of the substrate, and polymerising the polymer precursor to provide a polymeric layer comprising a polymer. A luminescent compound precursor may be provided within the layer comprising the polymer precursor and thus may participate in the polymerisation, so that the luminescent compound becomes incorporated in the polymeric layer as it is formed.

A luminescent compound precursor is a compound which can be copolymerised with a polymer precursor. The polymer thus formed comprises structural units derived from the luminescent compound precursor and comprising the luminescent compound. Typically, therefore, a luminescent compound precursor comprises the luminescent compound covalently bound to a polymerisable moiety. Where the luminescent compound is itself capable of being copolymerised with the polymer precursor to provide a polymer comprising structural units including the luminescent compound, the luminescent compound precursor may be the luminescent compound itself.

For example, step (c) may comprise providing a polymeric layer comprising a polymer chemically bound to the surface functional groups, wherein a luminescent compound is immobilised within the polymeric layer, by disposing a layer comprising a polymer precursor and a luminescent compound precursor on the surface of the substrate, and copolymerising the polymer precursor and the luminescent compound precursor.

It is particularly preferred to incorporate the luminescent compound into the polymer by copolymerisation with the polymer precursor as this can lead to excellent uniformity of distribution of the luminescent compound throughout the polymeric layer. This is desirable as, if multiple optical components are cut from the substrate, it is useful to ensure that those optical components have essentially identical or identical polymers thereon and hence have essentially identical or identical optical properties.

As explained above, it is also advantageous to incorporate the surface functional groups in the polymeric layer by copolymerisation. It is therefore particularly preferred to incorporate both the surface functional groups and the luminescent compound into the polymer by copolymerisation. This single-step process is highly convenient. Moreover, it produces a polymer which is strongly attached to the substrate and has excellent uniformity of distribution of the luminescent compound throughout the polymer.

Preferably, therefore, step (c) comprises disposing a layer comprising a polymer precursor and a luminescent compound precursor on the surface of the substrate and then terpolymerising the polymer precursor, the luminescent compound precursor and the surface functional groups. Preferably, the layer comprising the polymer precursor and the luminescent compound precursor has a uniform thickness. Accordingly, step (c) may comprise disposing the layer comprising a polymer precursor and a luminescent compound precursor on the surface of the substrate by spin-coating.

Substrate

The substrate is optically transmissive. By "optically transmissive" is meant that the substrate is transparent to visible light. Visible light is generally taken to mean light having a wavelength of from 400 to 700 nm. Of course, the substrate may be transparent to light outside the visible range. Typically, the substrate allows at least 90% of incident visible light to pass through it, for instance at least 95% or at least 98%.

Any suitable optically transmissive substrate may be used. In some embodiments, the substrate comprises or consists of glass. However, glass has a lower flexibility and greater susceptibility to shattering than other known optically transmissive materials.

More preferably, therefore, the substrate comprises an optically transmissive polymer. The polymer may be a silicon-based polymer or a carbon-based polymer. Most preferably, the substrate comprises PEEK, PET or PMMA. For example, the substrate may consist of one of PEEK, PET or PMMA.

The substrate may be of any shape or size. Preferably, the substrate is non-fluorescent. Also preferably, the analyte(s) of interest have a low solubility or are not soluble in the substrate.

For example, the substrate may have dimensions such the substrate produced by the process described above is suitable for use as an optical component without further cutting or machining. In one embodiment, the substrate may be dimensioned to fit onto the end of an optical waveguide such as an optical fibre or a bundle of optical fibres.

As explained above, in a preferred embodiment, a polymeric layer of uniform thickness is chemically bound to the surface functional groups on the polymeric layer. It is easiest to achieve this where the substrate is in the form of a sheet, for example by spin-coating of a layer comprising a polymer precursor onto the substrate. In a preferred embodiment, therefore, the substrate is in the form of a sheet. Where the substrate is in the form of a sheet, the largest dimension of the substrate in the plane of the sheet greatly exceeds the largest dimension of the substrate perpendicular to the plane of the sheet.

The largest dimension of the substrate perpendicular to the plane of the substrate where the substrate is in the form of a sheet may be referred to as the thickness of the substrate. The substrate may have any thickness.

Generally, the optical transmissivity of a substrate will decrease as its thickness increases. Accordingly, in order to fulfil the requirement that the substrate is optically transmissive, the substrate typically does not have a very large thickness. For instance, the substrate may have a thickness of up to about 20 mm. Preferably, the substrate has a thickness of up to about 20 mm, for instance up to about 5 mm.

In order to provide good mechanical strength and rigidity, it is also preferred that the substrate is not too thin. Typically therefore the substrate has a thickness of at least 100 nm, preferably at least 500 nm, and more preferably at least 1 mm.

In a particularly preferred embodiment, the thickness of the substrate is from about 1 mm to about 5 mm, for example about 2 mm, about 3 mm or about 4 mm.

In a preferred embodiment of the invention, the substrate is spin-coated with a layer comprising a polymeric precursor. Thus, in some embodiments, the substrate has dimensions suitable for spin-coating. For example, the substrate may be in the form of a disc having a diameter (that is, a largest dimension) of from about 5 to 5000 mm; preferably from about 10 to 2500 mm; more preferably from about 50 to 2500 mm. Ideally, the substrate has a diameter of 50 to 500 mm, for example 100 mm, 150 mm or 200 mm.

Further Process Steps

The product comprising a substrate and polymeric layer produced by a process as described above may itself be useful as an optical component without further modification. However, one or more further process steps may be performed on the product of the above-described process. These further process steps may be performed in any order.

As explained above in detail, it is desirable to ensure that the polymeric layer has a uniform thickness. This is conveniently achieved by forming the polymeric layer by polymerising a layer comprising a polymer precursor and having a uniform thickness. The polymer precursor is easy to manipulate. However, it is also possible to process the polymeric layer in order to provide a polymeric layer having uniform thickness. This may be achieved by, for example, spreading or cutting the polymeric layer.

In some embodiments, therefore, the process comprises spreading the polymeric layer over the surface to provide a polymeric layer having uniform thickness.

In some embodiments, the process comprises washing the polymeric layer after step (c). Once the polymeric layer is chemically bound to the surface functional groups, the polymeric layer can easily be washed without displacing it from the substrate. The washing step removes unreacted species such as unreacted polymer precursor, luminescent compound precursor or luminescent compound predecessor, and by-products of polymerisation. A washing step is particularly convenient where the polymer is a hydrogel, as the polymer can be washed with water.

The process may comprise drying the polymeric layer after step (c) to remove excess solvent. For example, the process may comprise drying the polymeric layer after step (c) to remove excess water. Where the process comprises washing the polymeric layer, the process typically also comprises drying the polymeric layer.

In some embodiments, the process may comprise disposing a filtering membrane on the polymeric layer. A filtering membrane is a membrane which selectively allows the passage of analyte into the polymeric layer, while preventing one or more undesired species from entering the polymeric layer. This selectivity can be achieved as the filtering membrane is typically a porous membrane comprising pores, and the sizes of the pores may be selected to allow the analyte through (as the analyte is generally very small) while preventing larger species from passing through. A filtering membrane is typically a gas-permeable membrane. In some embodiments, the filtering membrane is also permeable to liquids. Preferably, a filtering membrane is impermeable to blood elements (for example platelets) and/or proteins. Such species could disadvantageously interfere with the interaction of the luminescent compound and the analyte, and so it is desirable to prevent them from entering the polymeric matrix.

Also preferably, a filtering membrane is hydrophobic. A hydrophobic filtering membrane can prevent the adsorption of proteins to the optical component when the optical components is exposed to a sample comprising proteins. This is advantageous as protein adsorption can block the optical component and impair its performance in an optical sensor.

A filtering membrane may have a further advantageous function of presenting a biocompatible interface. This may be useful where the optical component is intended to be contacted with a biological sample in use, particularly a biological sample which is intended to be returned to the body of a patient.

A suitable example of a filtering membrane is a microporous membrane. A microporous membrane typically has a pore size of the order of microns, for example from 0.01 microns to 1000 microns, usually from 0.1 microns to 10 microns, preferably from 1 micron to 5 microns. A typical microporous membrane has a pore size about 0.1 to 0.4 microns. The pore size determines the size of species which may pass through the membrane. Accordingly, a microporous membrane typically prevents micron-sized species from passing through. For example, a microporous membrane may prevent species having a diameter of greater than 10 microns, or greater than 5 microns, preferably greater than 1 micron from passing through.

Another example of a filtering membrane is a nanoporous membrane. A nanoporous membrane typically has a pore size of the order of nanometres, for example from 0.01 nm to 1000 nm, usually from 0.1 nm to 100 nm. The pore size determines the size of species which may pass through the membrane. Accordingly, a nanoporous membrane typically prevents nanometer-sized species from passing through. In practice, a nanoporous membrane may prevent species having a molecular weight of greater than 20 kDa, for example greater than 15 kDa, from passing through. Usually, a nanoporous membrane has a molecular weight cutoff (i.e. a maximum molecular weight species which is allowed through) of at least 1 kDa, preferably at least 2 kDa, for example at least 5 kDa. Typically the molecular weight cutoff of a nanoporous membrane is from about 2 kDa to about 15 kDa.

A filtering membrane may be disposed on the polymeric layer after step (c). However, a filtering membrane may also be disposed on the substrate earlier in the process. In embodiments where the polymeric layer is generated in situ on the substrate by polymerisation of a polymer precursor, the process may comprise disposing a filtering membrane on the surface of the substrate after step (b). In such embodiments, a filtering membrane may be disposed on the layer comprising a polymer precursor (optionally together with a luminescent compound precursor and other components such as a crosslinker or polymerisation initiator) before polymerisation is initiated. In such embodiments, the filtering membrane may be soaked in the same medium as the medium forming the layer comprising the polymer precursor; this ensures that, when polymerisation occurs, the polymer is formed penetrating the pores of the filtering membrane and adhering the filtering membrane to the polymeric layer.

The process may comprise disposing more than one filtering membrane on the polymeric layer.

Notably, the process may comprise cutting an optical component from the substrate. For example, the process may comprise cutting two or more optical components from the substrate. It is particularly advantageous to cut two or more optical components from the substrate as this allows a plurality of optical components to be produced which are known to have identical thicknesses of polymeric matrix thereon, and hence identical optical responses when used in an optical sensor.

Figure 2:
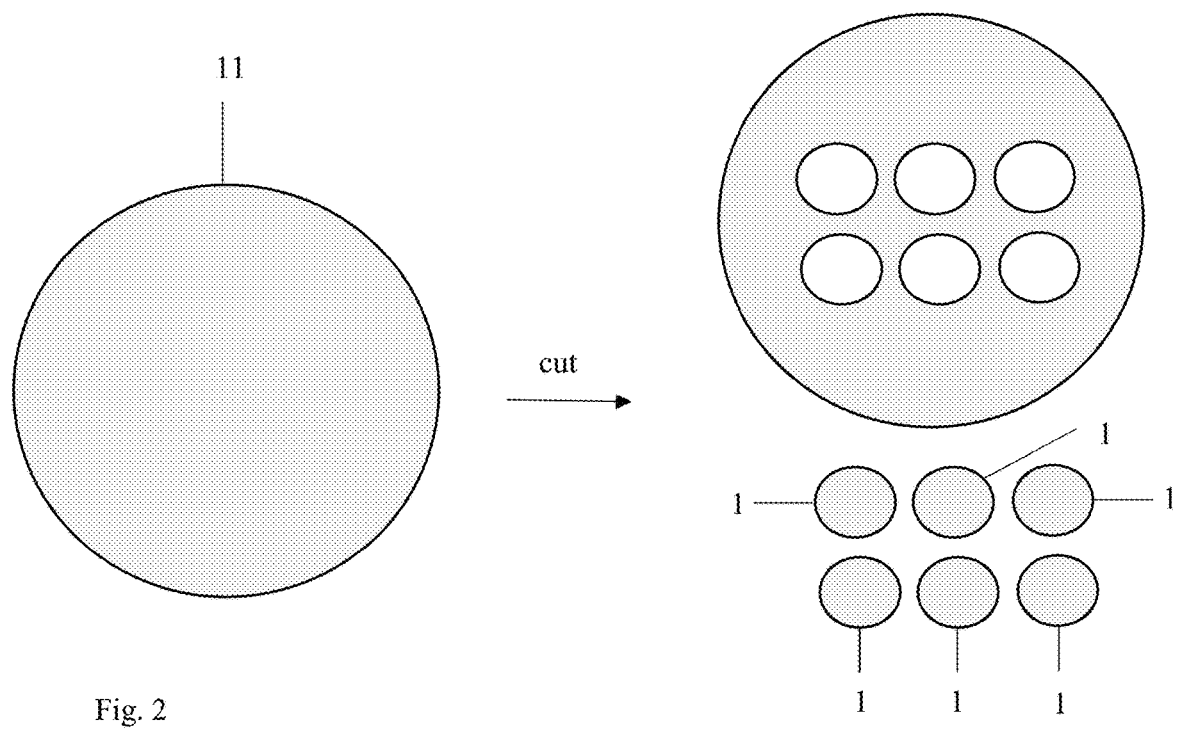
FIG. 2 provides a schematic representation (top view) of the cutting of six identical optical components from a product of a process according to the invention.

The cutting of two or more optical components from the substrate is illustrated schematically in FIG. 2. This shows a disc-shaped product 11 produced by a process as described above, from which six identical optical components 1 are cut out. The schematic is a top view and so the substrate and polymeric layer present in the product and optical components are not separately visible.

An optical component may be cut out by any means. For example, an optical component may be punched or drilled out. These processes are highly scalable, allowing a large number of optical components to be produced. In a preferred embodiment, therefore, the process comprises punching or drilling two or more optical components from the product of the above-described process.

Optical Component

The invention also provides an optical component, which could be produced by the above-described process. Accordingly the invention provides an optical component comprising: an optically transmissive substrate which has a surface; a polymeric layer comprising a polymer chemically bound to surface functional groups on the surface; and a luminescent compound immobilised within the polymeric layer.

The optically transmissive substrate, the polymeric layer, the polymer, the surface functional groups and the luminescent compound are as described above.

The optical component is typically dimensioned to fit in an optical sensor. For instance, it is typically dimensioned to fit over the end of an optical fibre which acts as a waveguide in a sensor, or over the end of a bundle of such optical fibres. Preferably, therefore, an optical component is disc-shaped. By disc-shaped is meant that the optical component is typically approximately in the shape of a cylinder wherein the diameter of the cylinder greatly exceeds its length along its axis of rotational symmetry. An optical component may have a diameter of from about 1 mm to about 5 mm, for example about 2 mm, about 3 mm or about 4 mm. The thickness of the substrate and the polymeric layer in the optical component are as described above.

Preferably, the optical component is obtained or obtainable by a process as described above.

The optical component may optionally comprise a filtering membrane disposed on the polymeric layer, wherein the filtering membrane is described above.

Process for Producing a Plurality of Optical Components

Although it is convenient to chemically bind the polymer to surface functional groups on the surface of the substrate, that is not necessary. A plurality of optical components having essentially identical or identical optical properties can be produced by cutting two or more optical components (i.e. a plurality of optical components) out of a substrate on which is disposed a polymeric layer of uniform thickness with a luminescent compound immobilised therein. Accordingly, the invention provides a process for producing a plurality of optical components, the process comprising:

A. providing a substrate which is optically transmissive and which has a surface;

B. providing a polymeric layer having a uniform thickness on the surface, wherein a luminescent compound is immobilised within the polymeric layer; and C. cutting two or more optical components from the substrate.

The substrate, the polymeric layer and the luminescent compound are as described above.

The step of cutting two or more optical components from the substrate produces two or more optical components each comprising the substrate having a surface, and a polymeric layer on the surface wherein a luminescent compound is immobilised within the polymeric layer.

The step of cutting two or more optical components from the substrate may be performed by any means, for example by punching or drilling the optical components from the substrate.

Each of the optical components produced is typically dimensioned to fit in an optical sensor. For instance, each optical component is typically dimensioned to fit over the end of an optical fibre which acts as a waveguide in a sensor. Preferably, therefore, each optical component is disc-shaped. Each optical component may have a diameter of from about 1 mm to about 5 mm, for example about 2 mm, about 3 mm or about 4 mm. The thickness of the substrate and the polymeric layer in the optical component are as described above.

In this embodiment, it is preferred that steps (A) and (B) include a process comprising steps (a), (b) and (c) as described in detail above. Preferably, therefore, the polymeric layer is covalently bound to surface functional groups on the surface of the substrate.

Optical Sensor

The optical component described above contains sensing chemistry which may be used in an optical sensor in order to detect an analyte. An optical sensor generates an optical signal which varies in the presence of an analyte, due to interaction of the analyte with a luminescent compound. In a typical optical sensor construction, the optical sensor may comprise an optical waveguide at the end of which is disposed a polymer in which a luminescent compound (such as described herein) is immobilised. The optical component of the present invention is an easily removable and replaceable part which can replace the polymer matrix attached to the end of an optical waveguide.

Accordingly, the invention provides an optical sensor comprising:
an optical component as described herein; and
an optical waveguide arranged to direct light onto the optical component.

Figure 3:
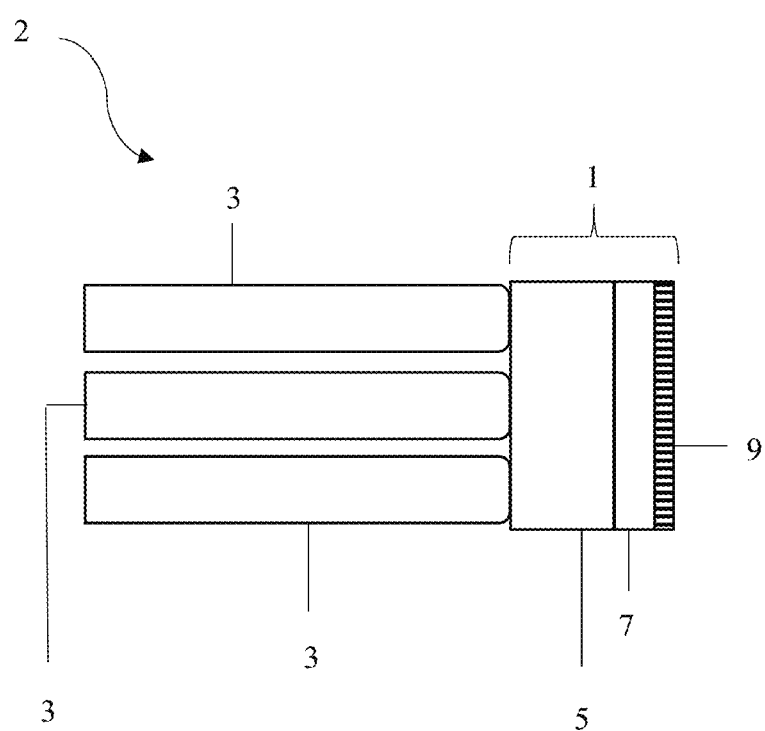
FIG. 3 is a cross-section of an optical sensor according to an embodiment of the invention.

A typical optical sensor 2 according to the invention is shown in FIG. 3.

The optical component 1 is typically arranged at an end of the optical waveguide 3.

Also typically, the optical waveguide 3 may be one of a number of optical waveguides 3 present in the optical sensor 2. The optical sensor 2 may for example comprise an optical component 1 as described herein and a plurality of optical waveguides 3 each arranged to direct light onto the optical component 1. The optical component 1 is typically arranged at an end of each of the optical waveguides 3.

The optical component 1 comprises a substrate 5, a polymeric layer 7 and optionally a filtering membrane 9. The optical component 2 is typically arranged such that the optically transmissive substrate portion of the optical component is disposed between the optical waveguide(s) and the polymeric layer portion of the optical component. This arrangement is shown in FIG. 3. This arrangement permits the polymeric layer (and, if present, the filtering layer thereon) to be exposed to the environment and hence accessible to any sample under test.

FIG. 3 illustrates an embodiment of the optical sensor 2 wherein the sensor comprises a bundle of three optical waveguides 3 (e.g. a bundle of three optical fibres) arranged to direct light onto an optical component 1. In practice, the optical sensor 2 may include one, two, three or more optical waveguides 3.

The optical waveguide(s) 3 is arranged to direct excitation light onto the optical component 1. Light emitted by the luminescent compound also passes through the optical waveguide(s) 3.

The optical waveguide(s) 3 may be in direct contact with the optical component 1. However, this is not necessary; in some embodiments, for example, the optical component 1 may contact the optical waveguide(s) 3 via a coating such as a layer or adhesive; in other embodiments, the optical component 1 may be separated from the optical waveguide(s) 3 via an air gap. Preferably, however, any air gap between the optical waveguide(s) 3 and the optical component 1 is minimised.

The optical component 1 may or may not be attached to the optical waveguide(s) 3. The optical component 1 may be attached to the optical waveguide(s) 3 via an adhesive, so that the optical component 1 and the optical waveguide 3 may be conveniently moved together. However, an adhesive layer presents an optical barrier. In other embodiments, therefore, the optical sensor 2 may comprise a housing (not shown in FIG. 3) which holds the optical component 1 and the optical waveguide(s) 3. For instance, the housing may hold the optical component 1 in contact with an end of the optical waveguide(s) 3.

The optical component 1 may comprise a filtering membrane 9, as shown in FIG. 3, although this is not necessary. Where the optical component 1 comprises a filtering membrane 9, the substrate 5 and the polymeric layer 7 are typically disposed between the optical waveguide(s) 3 and the filtering membrane 9 in the optical sensor.

In use, the optical component 1 (and specifically the polymeric layer 7 therein) contacts a sample (not shown in FIG. 3). Where the optical component 1 comprises a filtering membrane 9 disposed on the polymeric layer 7, the filtering membrane 9 is configured such that an analyte present in the sample may pass through the filtering membrane 9 in order to contact the polymeric layer 7. Thus, the filtering membrane 9 can prevent the passage of other components of the sample into the polymeric layer 7.

The optical sensor 2 is suitable for detecting whether or not an analyte is present in a sample. The optical sensor 2 may also be suitable for quantifying the amount of an analyte in a sample. The sample may be any fluid. Exemplary samples include buffers, and biological samples such as saliva or blood. In a preferred embodiment, the sample is a blood sample, for instance a blood sample taken from a human patient. Thus, in a preferred embodiment, the optical sensor 2 is a sensor for detecting an analyte in blood.

Where the sample is a biological sample, the sample is typically an ex vivo sample; that is, the sample is typically outside the human or animal body.

The optical waveguide(s) 3 may be any optically transmissive material. Typically, the waveguide 3 comprises or consists of an optical fibre. Optical fibres use total internal reflection to prevent light being lost from the fibre. This means light can be efficiently carried to and from the luminescent compound, improving the signal and providing for higher-quality and more reliable measurements.

Optionally, the optical sensor 2 may comprise a reflector configured to reflect light emitted by the luminescent compound into the optical waveguide(s). The reflector, where present, increases the proportion of light emitted by the luminescent compound which can be collected by the waveguide and subsequently detected. The reflector may be disposed on the optical component 1. For instance, the reflector may be disposed on the opposite side of the filtering membrane 9 (where present), to the polymeric layer 7.

Where the reflector is disposed on the optical component 1, it must be permeable to the analyte. Alternatively, the optical sensor 2 may comprise a reflector which is separate to the optical component 1. Suitable materials which may be used as reflectors include polysulfones (PSU), polyethersulfones (PESU), and polyphenylsulfones (PPSU). Polysulfones are preferred. It would also be possible to use other reflecting compounds such as silicon containing titanium oxide, or barium sulfate.

The optical sensor 2 may further comprise a light source configured to provide excitation light to the luminescent compound. The light source may be any light source capable of emitting light at the wavelengths and intensities required to excite the luminescent compound. For example, the light source may comprise a laser diode.

The optical sensor 2 may further comprise a detector configured to detect light emitted by the luminescent compound through the optical waveguide 3. The detector may be any device capable of producing a signal in response to receiving light at the wavelengths emitted by the luminescent compound. For example, the detector may comprise a charge-coupled device, an active-pixel sensor, a photodiode, or photoresistor.

Some or all of the optical sensor 2 may be disposable. This is convenient in clinical contexts, where optical sensor may be contacted with a biological sample inside or taken from a patient. In such cases, the part of the optical sensor 2 which contacts the biological sample should be sterile and cannot be reused between patients. For example, the optical component 1 may be disposable while the detector and/or light source and/or optical waveguide(s) 3 can be re-used.

The optical sensor 2 may form part of an optical sensing system which further comprises a control system. The control system may be configured to cause the light source to emit light, and optionally to activate the detector if necessary. The optical sensing system may further comprise an analysis system. The analysis system may be configured to determine whether an is present in the sample under test. In particular, the analysis system may be configured to quantify the amount of the analyte in the sample under test.

The optical sensor and optical sensing system described herein can be used to provide rapid, real-time measurements of the amount of analyte in a sample.

Process for Producing Optical Sensor

The invention provides a process for producing an optical sensor as described above. Thus, described herein is a process for producing an optical sensor as described above, the process comprising:

provided an optical component comprising a substrate, a polymeric layer and a luminescent compound within the polymeric layer by a process as described herein; and arranging an optical waveguide to direct light onto the optical component.

The step of arranging an optical waveguide to direct light onto the optical component may comprise arranging an end of the optical waveguide adjacent to, for example in contact with, the substrate of the optical component.

The process may comprise arranging a plurality of optical waveguides, for example a bundle of optical waveguides, to direct light onto the optical component.

In a particular example, the step of arranging one or more optical waveguides to direct light onto the optical component may comprise providing a housing which is dimensioned to contain all or part of the optical waveguide(s) and the optical component, and disposing all or part of the optical waveguide(s) and the optical component in the guide. The optically transmissive substrate portion of the optical component is disposed between the optical waveguide(s) and the polymeric layer portion of the optical component The process for producing an optical sensor may be repeated to provide two or more sensors. In this case, it is preferred that each optical component comprises a polymeric layer of essentially identical thickness, and essentially identical chemical composition. By "essentially identical thickness" is meant that the thickness of the polymeric layer in each optical component differs by no more than 10% from the mean thickness measured across each optical component. Preferably the said thickness differs by no more than 5%, more preferably by no more than 1%. Similarly, by "essentially identical chemical composition" is meant that the molar concentration of luminescent compound in the polymeric layer of each optical component differs by no more than 10% form the mean molar concentration measured across each optical component. Preferably the said concentration differs by no more than 5%, more preferably by no more than 1%.

Analysis of a Sample

The optical sensor described herein can be used to detect whether or not an analyte is present in a sample. The optical sensor can further be used to determine the amount of an analyte in a sample. The analyte is as described above.

This can be achieved by providing excitation light to the luminescent compound and detecting either the luminescent light emitted by the luminescent compound, or the absorption of light by the luminescent compound. It is preferred to use the sensor to detect luminescent emission. This is because the path length of light through the sensing region of the optical sensor is generally too small to allow strong absorbance. In particular, it is preferred to detect fluorescent light emitted by the luminescent compound, as the intensity of fluorescence emission is generally greater than the intensity of phosphorescent emission.

Thus, described herein is a process for detecting and/or quantifying the amount of an analyte in a sample, the process comprising:

contacting an optical sensor as described herein with a sample;

providing excitation light to the luminescent compound through the optical waveguide; and detecting luminescent light emitted from the luminescent compound through the optical waveguide.

Preferably, the luminescent compound comprises a fluorophore capable of emitting fluorescent light, and the process comprises detecting fluorescent light emitted from the fluorescent compound through the optical waveguide.

Detection of luminescent light (such as fluorescent light) may involve detection of light of a single wavelength, or detection of a range of wavelengths. For instance, luminescent emission across the whole of the visible spectrum may be detected.

Detection of luminescent light may involve detecting the intensity of emitted light. Alternatively the process may involve measuring the lifetime of the luminescent compound, particularly the fluorescence lifetime of the luminescent compound.

The method may comprise an initial step of calibrating the optical sensor.

The method may comprise a subsequent calculation step, involving comparing the detected emission intensity or lifetime to a calibration curve in order to determine the amount of analyte in the sample.

An optical measurement is performed rapidly, typically taking less than a second. Moreover, the sensor typically has a very rapid response time as the optical component is small and does not act as a reservoir for the analyte. Further, the optical sensor does not consume the analyte or generate any by-products. Accordingly, the sensor may be placed in contact with a biological sample (such as saliva or blood) which is inside the body or a patient or more usually is removed from and returned to the body of a patient. All these factors mean that the sensor is extremely well-suited to perform continuous measurements on a sample, particularly a biological sample, for long periods of time.

The process may be a process for continuously detecting and/or quantifying the amount of the analyte in the sample. For example, the process may involve continuously exposing the optical sensor to the sample for an exposure period of at least ten minutes;

providing excitation light to optical component continuously or intermittently throughout the exposure period through the optical waveguide; and detecting luminescent light emitted from the luminescent compound through the optical waveguide continuously or intermittently throughout the exposure period.

The exposure period is preferably at least 1 hour. For instance, the exposure period may be at least for hours, typically up to 100 hours. The measurement method may therefore be used where it is important to monitor a biological sample (such as blood) for long periods, for instance during dialysis or open-heart surgery

EXAMPLES

1. General Process for Producing an Optical Component

An exemplary method of producing an optical component is described. A sheet of polyethylene terephtalate (PET) with a thickness of 2-10 mm but ideally 3 mm is used as the substrate. The sheet has a diameter of 150 mm. The first stage is to place the sheet within a plasma arc machine containing nitrogen and hydrogen; this produces amine groups (reactive groups) on the surface of the substrate. The amine groups are then reacted with an unsaturated acid chloride, for example acryloyl chloride, to produce surface functional groups of the formula —NHCO—CH=CH$_2$:

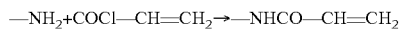

—NH$_2$+COCl—CH=CH$_2$→—NHCO—CH=CH$_2$

All subsequent steps are carried out under inert conditions.

The 150 mm PET waveguide disc with the monomeric functionalised surface is placed into a spin coating machine, or modified centrifuge, and approximately 0.5 g of an optimised degassed mixture of the luminescent compound precursor and polymer precursor (which is a hydrogel monomer) is provided on the surface. This mixture may also contain a dimer crosslinker and polymerisation initiator. This quantity is enough material to give a 30 micron thick layer comprising the polymer precursor on the surface of the substrate. The PET disc is spun so that an even coating of the mixture is applied. Once carried out the coated 150 mm PET disc is removed from the spin coating machine and the layer comprising the polymer precursor is thermally cured at an optimised temperature.

By-products from the polymerisation are washed out of the polymeric layer by prolonged washing with water and the polymeric layer is then dried.

A plurality of discs, each 2-10 mm in diameter and typically 3 mm diameter are punched or drilled with a hollow drill from the substrate produced as above.

2. Exemplary Method of Producing an Optical Component

An optical component was generated as follows.

Step 1—a polyethylene terephthalate (PET) sheet was washed with isopropyl alcohol (IPA) and dried. The surface of the PET sheet was then treated to produce reactive groups on the surface of the PET sheet by aminolysis. Specifically, 2,2'-(ethylenedioxy)bis(ethyamine) (0.5 ml per cm$^2$) was then added to cover the surface of the PET sheet and was left at room temperature for 30 minutes. The PET sheet was then washed with IPA and dried. This produced —NR$_2$ groups such as —NH$_2$ groups attached to the surface. In particular, —NH$_2$ groups attached to the surface by an —NH—(CH$_2$)$_2$—O—(CH$_2$)$_2$—O—(CH$_2$)$_2$— linker were produced on the surface.

Step 2—surface functional groups were produced on the surface as follows. The surface of the amine functionalised PET sheet was covered with diisopropylethyleneamine (DIPEA), (0.5 ml per cm$^2$) and methacrylic anhydride (0.43 ml per cm$^2$) and was left at room temperature for 4 hours. The PET was then washed with IPA and dried. This produced surface functional groups comprising C=C double bonds attached to the surface of the PET sheet. In particular, surface functional groups of formula -L$_1$-X-L$_2$-C(=O)R were produced wherein L$_1$ was —NH—(CH$_2$)$_2$—O—(CH$_2$)$_2$—O—(CH$_2$)$_2$—, X was NH, L$_2$ was a covalent bond and R was a methyl group.

Step 3—a monomer mixture comprising (i) a polymer precursor, dimethylacrylamide (971 mg); (ii) a pH-sensitive monomer DHDS (dihydroxypyrene disulfonate, shown below)

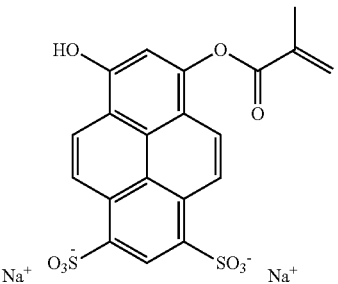

which comprises a fluorophore (5 mg); (iii) PEG-DMA-600 (84 mg); (iv) an initiator, AIPD (4 mg); and (v) water, 1.728 ml was added to the functionalised surface of the PET sheet so as to form a thin layer. This layer comprising the polymer precursor is referred to as the "monomer mix". This was heated in an oven at 60° C. for 1 hour, causing copolymerisation of the surface functional groups with the polymer precursor and the pH-sensitive monomer and thus producing a polymeric layer comprising a hydrogel and a fluorophore chemically bound to the surface of the PET sheet. The optical component thus produced was then submerged in PBS so as to remove any unreacted monomers.

Figure 4:
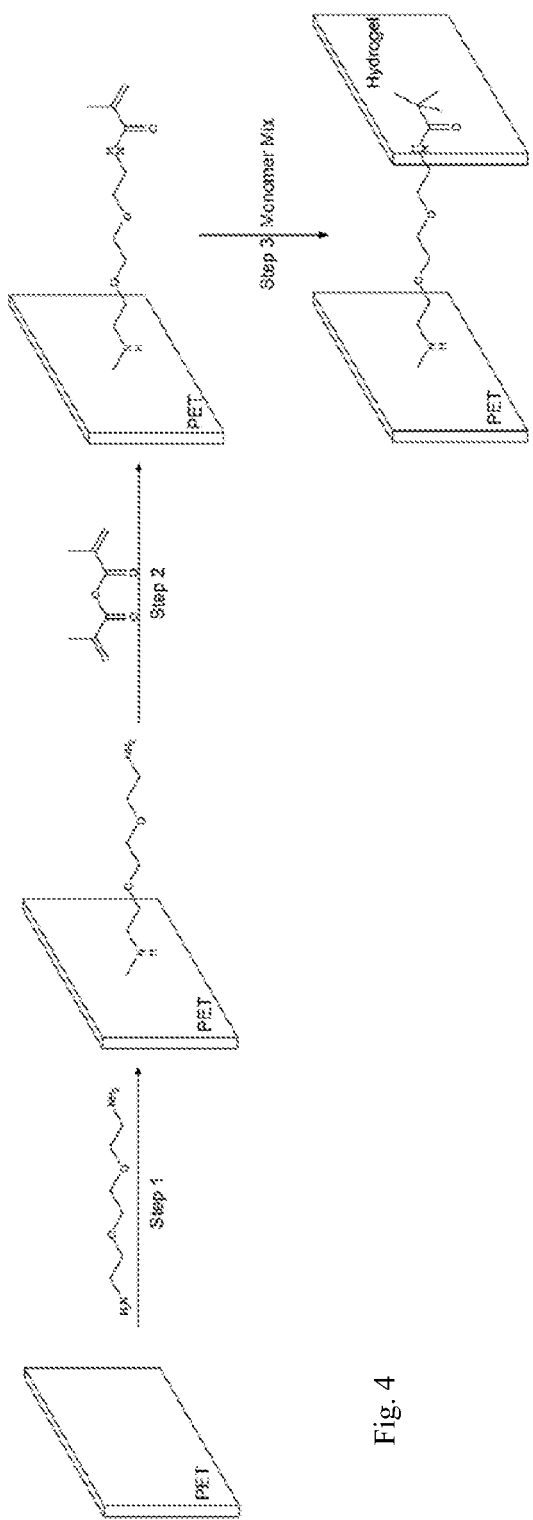
FIG. 4 is a schematic representation of a process for producing an optical component described herein.

A schematic diagram of the process according to this example is shown in FIG. 4.

3. Testing of the Optical Component

Figure 5:
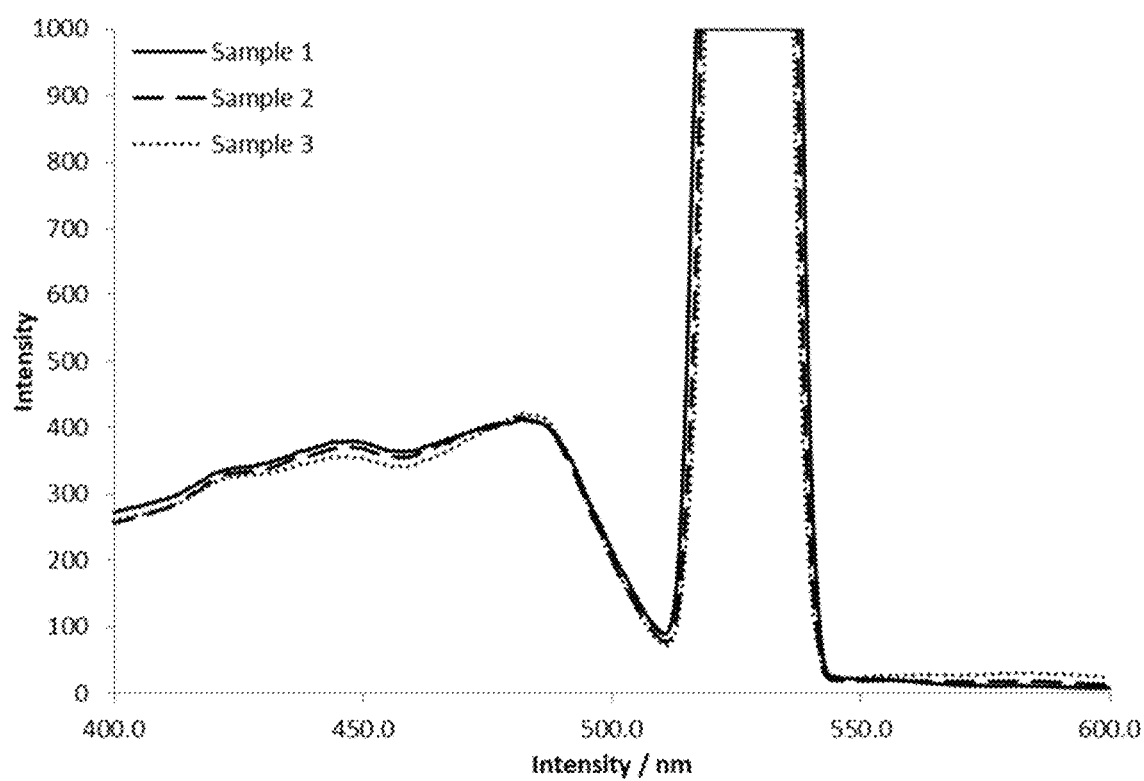
FIG. 5 shows the emission spectrum of three optical components produced by a process as described herein upon exposure to visible light.

The optical component produced as described in Example 2 was tested as follows. Three samples were cut from the PET sheet. Each sample was coupled to an optical component (an optical waveguide), producing an optical sensor. These samples were exposed to a solution buffered to pH 7.3. The samples were irradiated with visible light (via the optical waveguide) in the range 400 nm to 600 nm, and the emission from the fluorophore in each sample piece at a wavelength of 525 nm was collected via the optical waveguide and detected. The emission spectrum of each of the three samples is shown, overlaid, in FIG. 5. These spectra have been normalised in order to account for any difference in mating between each optical component and the respective optical waveguide, which may have collected slightly different quantities of emitted fluorescent light.

It can immediately be seen that the three samples have highly uniform emission spectra. The relative intensity of emission at each wavelength in the range 400 to 600 nm is essentially identical for each sample: this is clear from the fact that the normalised spectra lie generally on top of one another.

As a further illustration of the excellent uniformity of the three samples cut from the functionalised PET sheet produced in Example 2, the fluorescence intensity of each sample at both 420 nm and 475 nm has been extracted and is shown in Table 1. The intensity ratio of the emission at each of these two wavelengths was calculated and is also shown in Table 1.

TABLE 1

Intensity at 420 and 475 nm and the ratio thereof

| Wavelength/nm | Sample 1 | Sample 2 | Sample 3 |
|---|---|---|---|
| 420 | 331.2 | 321.5 | 317.4 |
| 475 | 397.9 | 400.6 | 393.3 |
| Ratio | 1.2 | 1.2 | 1.2 |

The ratio calculated for all three samples is consistent for all samples, demonstrating that the method of the invention can produce optical components having highly consistent optical properties.

The invention claimed is:

1. A process for producing a plurality of optical components, the process comprising:
   A. providing a substrate which is optically transmissive and which has a surface;
   B. providing a polymeric layer of uniform thickness on the surface, wherein a luminescent compound is immobilised within the polymeric layer; and
   C. cutting two or more optical components from the substrate.

2. The process according to claim 1 wherein after the step (A) of providing the substrate which is optically transmissive and which has the surface, the process further comprises (b) functionalising the surface of the substrate to produce surface functional groups thereon,
   wherein the polymeric layer comprises a polymer, and
   wherein the step (B) of providing the polymeric layer comprises chemically binding the polymer to the surface functional groups.

3. The process according to claim 2 wherein functionalising the surface of the substrate comprises
   (b)(i) treating the surface to produce reactive groups on the surface; and
   (b)(ii) reacting the reactive groups with a surface functional group precursor to produce the surface functional groups.

4. The process according to claim 3 wherein the reactive groups comprise one or more of a radical, an anion, an electrophile or a nucleophile.

5. The process according to claim 3 wherein the reactive groups comprise one or more of —OR, —O$^-$, —COOR and —NR$_2$;
   each R is independently selected from H, or C$_{1-6}$ alkyl, C$_{2-6}$ alkenyl or C$_{2-6}$ alkynyl which may be optionally substituted; and
   each of which is attached to the surface of the substrate either directly or via a linker -L$_{1-}$.

6. The process according to claim 3 wherein the surface functional group precursor comprises an unsaturated bond and a leaving group.

7. The process according to claim 3 wherein the surface functional group precursor is selected from methacryloyl chloride, acryloyl chloride, methacryloyl anhydride and acryloyl anhydride.

8. The process according to claim 2 wherein functionalising the surface of the substrate comprises exposing the surface of the substrate to a plasma, an amine or an oxidant.

9. The process according to claim 2 wherein the surface functional groups comprise a polymerisable group, preferably a C=C bond.

10. The process according to claim 2 wherein the surface functional groups are groups of formula -L$_1$-X-L$_2$-CR=CR$_2$, -L$_1$-X-L$_2$-C≡CR, or -L$_1$-X-L$_2$-C(=O)R, wherein
    X is O or NR;
    each R is independently selected from H, or C$_{1-6}$ alkyl, C$_{2-6}$ alkenyl or C$_{2-6}$ alkenyl which may be optionally substituted;
    L$_1$ is a linker consisting of one or more groups each independently selected from a covalent bond, —O—, —NR'— and —CR'$_2$—, wherein R' is H or C$_{1-4}$ alkyl; and
    L$_2$ is a selected from a covalent bond, or a carbonyl group, or C$_{1-6}$ alkylene, C$_{2-6}$ alkenylene or C$_{2-6}$ alkynylene which may be optionally substituted.

11. The process according to claim 2 wherein the step of providing the polymeric layer comprises disposing a layer comprising a polymer precursor on the surface of the substrate and then polymerising the polymer precursor.

12. The process according to claim 11 wherein the polymer precursor is copolymerised with the surface functional groups.

13. The process according to claim 11 wherein the layer comprising the polymer precursor has a uniform thickness, and optionally wherein the layer comprising a polymer precursor is disposed on the surface of the substrate by spin-coating.

14. The process according to claim 1 wherein the luminescent compound comprises a fluorophore, and the fluorescence emission spectrum of the fluorophore varies in the presence of an analyte; and/or wherein the luminescent compound comprises a receptor moiety.

15. The process according to claim 1 wherein the luminescent compound is immobilised within the polymeric layer by suspending the luminescent compound within the polymeric layer or chemically binding the luminescent compound to the polymeric layer.

16. The process according to claim 2 wherein the step (B) comprises disposing a layer comprising a polymer precursor and a luminescent compound precursor on the surface of the substrate and copolymerising the polymer precursor and the luminescent compound precursor.

17. The process according to claim 16 wherein step (B) comprises disposing a layer comprising a polymer precursor and a luminescent compound precursor on the surface of the substrate and then terpolymerising the polymer precursor, the luminescent compound precursor and the surface functional groups.

18. The process according to claim 1 wherein the substrate is in the form of a sheet, and/or wherein the substrate has a thickness of up to about 10 mm.

19. The process according claim 1 wherein the polymeric layer has a thickness of from about 1 to about 200 µm, preferably from about 10 to about 100 µm.

20. The process according to claim 1 wherein the polymer comprised in the polymeric layer is a hydrophilic polymer, preferably a hydrogel.

21. The process according to claim 1 wherein the step of providing a polymeric layer comprises spreading the polymeric layer over the surface to have a uniform thickness.

22. The process according to claim 1 wherein the two or more optical components each comprise a polymeric layer of identical thickness and identical composition.

23. An optical component comprising: an optically transmissive substrate which has a surface; a polymeric layer of uniform thickness comprising a polymer chemically bound to surface functional groups on the surface; and a luminescent compound immobilised within the polymeric layer.

24. The optical component according to claim 23 wherein the optical component is obtained or obtainable by a process comprising:
   a) providing a substrate which is optically transmissive and which has a surface;
   b) functionalising the surface of the substrate to produce surface functional groups thereon; and
   c) providing a polymeric layer comprising a polymer chemically bound to the surface functional groups, wherein a luminescent compound is immobilised within the polymeric layer.

25. An optical sensor comprising:
   the optical component as defined in claim 23; and
   an optical waveguide arranged to direct light onto the optical component.

* * * * *